(12) United States Patent
Camras et al.

(10) Patent No.: US 9,186,274 B2
(45) Date of Patent: *Nov. 17, 2015

(54) METHOD AND APPARATUS FOR REDUCING INTRAOCULAR PRESSURE

(75) Inventors: Carl B. Camras, Omaha, NE (US); Nancy Louise Camras, legal representative, Omaha, NE (US); Lucinda J. Camras, Omaha, NE (US)

(73) Assignee: CAMRAS VISION INC., Research Triangle Park, NC (US)

( * ) Notice: Subject to any disclaimer, the term of this patent is extended or adjusted under 35 U.S.C. 154(b) by 256 days.

This patent is subject to a terminal disclaimer.

(21) Appl. No.: 12/546,864

(22) Filed: Aug. 25, 2009

(65) Prior Publication Data

US 2010/0057055 A1    Mar. 4, 2010

Related U.S. Application Data

(63) Continuation-in-part of application No. 11/063,623, filed on Feb. 23, 2005, now Pat. No. 7,641,627.

(51) Int. Cl.
*A61B 19/00* (2006.01)
*A61F 9/007* (2006.01)

(52) U.S. Cl.
CPC .................................. *A61F 9/00781* (2013.01)

(58) Field of Classification Search
USPC .......... 604/7–10, 264, 30, 6.09, 6.1; 606/153, 606/108
See application file for complete search history.

(56) References Cited

U.S. PATENT DOCUMENTS

| 4,886,488 | A |   | 12/1989 | White |       |
|-----------|---|---|---------|-------|-------|
| 5,127,901 | A |   | 7/1992  | Odrich |      |
| 5,300,020 | A |   | 4/1994  | L'Esperance, Jr. | |
| 5,346,464 | A | * | 9/1994  | Camras | 604/9 |
| 5,743,868 | A |   | 4/1998  | Brown et al. | |
| 5,807,302 | A |   | 9/1998  | Wandel | |
| 5,830,173 | A | * | 11/1998 | Avery et al. | 604/9 |
| 5,882,327 | A | * | 3/1999  | Jacob | 604/8 |
| 6,537,241 | B1 |  | 3/2003  | Odland | |
| 6,558,342 | B1 |  | 5/2003  | Yaron et al. | |

(Continued)

*Primary Examiner* — Leslie Deak
(74) *Attorney, Agent, or Firm* — Womble Carlyle Sandridge & Rice, LLP

(57) ABSTRACT

A drainage apparatus is disclosed to reduce intraocular pressure in an eyeball that includes an anterior chamber having aqueous humor disposed therein, a cornea and a surrounding marginal limbus by which the cornea is continuous with a scleral layer and a conjunctival layer disposed on an exposed surface of the eyeball and under eyelids, the apparatus comprising an inlet assembly configured to be disposed at the anterior chamber of the eyeball, an outlet assembly configured to be disposed at the external surface of the eyeball, the assembly having a central chamber, a tube extending between the inlet and outlet assemblies and configured to promote fluid communication between the inlet and outlet assemblies, and control means disposed within the outlet assembly for controlling a flow of aqueous humor through the tube from the anterior chamber of the eyeball to the external surface of the eyeball, the control means further comprising a replaceable filter disposed within the central chamber of the outer member to prevent intraocular infection, the filter having a medicinal agent applied thereto for preventing occlusion of the filter or bacterial contamination by inhibiting at least one of the formation of fibrotic membranes, inflammatory membrane, or bacterial adhesions or biofilms, thereby preventing increased of intraocular pressure or infection.

22 Claims, 19 Drawing Sheets

(56) References Cited

U.S. PATENT DOCUMENTS

| | | |
|---|---|---|
| 6,595,945 B2 | 7/2003 | Brown |
| 6,881,198 B2 | 4/2005 | Brown |
| 7,135,009 B2 * | 11/2006 | Tu et al. ............... 604/8 |
| 7,641,627 B2 * | 1/2010 | Camras et al. ............... 604/9 |
| 2004/0249441 A1 * | 12/2004 | Miller et al. ............ 623/1.15 |
| 2007/0254005 A1 | 11/2007 | Pathak et al. |
| 2008/0228127 A1 * | 9/2008 | Burns et al. ............... 604/9 |

* cited by examiner

METHOD AND APPARATUS FOR REDUCING INTRAOCULAR PRESSURE

CROSS REFERENCE TO RELATED APPLICATION

This application is a continuation-in-part of Patent Application No. 11/063,623, filed Feb. 23, 2005.

BACKGROUND OF THE INVENTION

The present invention relates to the field of medical technology, particularly to an apparatus to be implanted in an eyeball for the treatment of glaucoma.

Glaucoma is one of the leading causes of blindness in the United States. It is estimated that two to three million people in the United States have some degree of visual loss resulting from glaucoma. While glaucoma is a medical condition which can be caused by several factors, excessive intraocular pressure is a major risk factor for developing glaucoma. Over time, excessive intraocular pressure can cause damage to the optic nerve resulting in gradual loss of vision and, in some cases, blindness. Excessive intraocular pressure is caused by an increase in the resistance to outflow of fluid, called aqueous humor, in the anterior chamber of the eyeball, which can be caused by a number of different factors including injury, the aging process, reaction to medication (such as corticosteroids), structural abnormalities within the eyeball, and a genetic predisposition.

Aqueous humor is a clear, watery fluid which is constantly circulated within the anterior chamber of the eyeball. It serves to nourish the cornea and lens and to provide the intraocular pressure necessary to maintain the shape of the eyeball. Aqueous humor exits the anterior chamber through a network of spongy tissue called the trabecular meshwork, which is located in the intersecting space (the angle) between the iris and the cornea. Increased intraocular pressure results when aqueous humor cannot drain properly or at an appropriate rate through the trabecular meshwork or other outflow pathways. The only proven treatment for glaucoma is to reduce intraocular pressure.

Increased intraocular pressure can in some cases be treated with appropriate medication. These medications are usually administered through pills or eye drops and work to either decrease the rate at which aqueous humor flows into the eyeball, or to increase the rate at which aqueous humor drains from the eyeball. However, as with any medication, patients experience different levels of response to the medication, and the side effects of some medications can become intolerable in certain individuals.

Surgical procedures are also employed to treat glaucoma. Certain procedures are referred to as "filtration" procedures, since the end goal of these particular surgical procedures is to increase the outflow of aqueous humor from the anterior chamber, thereby reducing intraocular pressure. Procedures focused on increasing the outflow of aqueous humor from the anterior chamber of the eyeball are theoretically more beneficial than those designed to decrease the production of aqueous humor, as over 95% of glaucomatous disease is a consequence of increased outflow resistance or reduced outflow rate rather than increased aqueous humor production or increased venous pressure distal to the outflow channels. Full thickness filtration surgical procedures involve the creation of an alternate route for the aqueous humor to flow from the anterior chamber of the eyeball into the subconjunctival space with the formation of a bleb—an area of limbal (anterior) filtration—which contains the aqueous humor. Guarded filtration surgical procedures, such as a trabeculectomy, involve the surgical creation of an opening which is covered by partial thickness sclera, from the anterior chamber into the subconjunctival space, thereby resulting in increased aqueous humor flow out of the anterior chamber. Unfortunately, the failure rate of filtration procedures is unacceptably high. In addition, postoperative intraocular pressure is almost always unstable and unpredictable. Initial overdrainage can lead to abnormally low intraocular pressure, known as hypotony, which can cause the eyeball to malfunction and delay the patient's postoperative recovery. Also, scarring or excessive resistance may occur in the subconjunctival, episcleral, or scleral regions (i.e., the sclerostomy site or surgical opening into the anterior chamber), thereby restricting the drainage.

Surgical procedures have also been used to reduce the amount of aqueous humor production within the eyeball. Ciliodestructive surgery, also known as cyclocryotherapy or cyclophotocoagulation, involves the use of either cryotherapy or a laser on the surface of the eyeball to reduce the production of aqueous humor. However, this procedure can cause a decrease in vision, and is usually used as a last resort when other procedures have failed.

Another method of treating intraocular pressure involves the use of drainage devices implanted within the anterior chamber as a means to drain aqueous humor while maintaining proper intraocular pressure. These devices typically incorporate a tube situated within the anterior chamber which drains aqueous humor from the anterior chamber into a surgically created posterior reservoir, called a fibrous capsule, formed around the scleral explant of the device underneath the conjunctiva. The aqueous humor which drains into the fibrous capsule is eventually reabsorbed by the body. Some of these drainage devices employ valve mechanisms to provide resistance to aqueous humor outflow. These valves have been shown to be unpredictable in their performance, resulting in excessive outflow of aqueous humor and possible hypotony. The valves can also become clogged and cease to function altogether, which results in an increase in intraocular pressure. Also, the fibrous capsule can become scarred or can develop excessive resistance, resulting in failure and a need for surgical revision. In addition, the insertion process for properly implanting these drainage devices within the eyeball can often be very complex and time consuming, increasing the duration of the surgical procedure itself and the postoperative recovery period for the patient.

Certain drainage devices have been developed to reduce intraocular pressure by draining aqueous humor from the anterior chamber to the external surface of the eyeball, as shown by U.S. Pat. No. 5,346,464 to Camras (see also U.S. Pat. Nos. 3,788,327 to Donowitz, 5,743,868 to R H Brown; 6,595,945 to Brown, 4,886,488 to White, 5,743,868 to Brown and 5,807,302 to Wandel). These drainage devices have the added benefit of not requiring the creation of a bleb or fibrous capsule for drainage. Therefore, the surgical outcome is not influenced by the problems associated with the formation and maintenance of a bleb or fibrous capsule, including subconjunctival scarring. The devices described in the prior art have not eliminated potential problems such as difficulty of proper insertion, failure of the device, unpredictable postoperative intraocular pressure without a means to compensate or adjust the device for optimal results, extrusion, tolerability (discomfort or irritation) and/or extended postoperative recovery time. Additionally, some of these devices do not adequately guard against the potential for infection by entry of microorganisms either through or around the device.

There exists a need in the art for a means to treat glaucoma which is predictable, which allows for the post-surgical adjustment of intraocular pressure, which results in long-term efficacy, which limits the risk of infection, which is comfortable for the patient, which is securely fixated preventing extrusion, and which can be properly inserted both quickly and easily. The present invention meets these needs.

SUMMARY OF THE INVENTION

A drainage apparatus is disclosed to reduce intraocular pressure in an eyeball that includes an anterior chamber having aqueous humor disposed therein, a cornea and a surrounding marginal limbus by which the cornea is continuous with a scleral layer and a conjunctival layer disposed on an exposed surface of the eyeball and under eyelids, the apparatus comprising an inlet assembly configured to be disposed at preferably the anterior chamber of the eyeball, an outlet assembly configured to be disposed at the external surface of the eyeball, the assembly having a central chamber, a tube extending between the inlet and outlet assemblies and configured to promote fluid communication between the inlet and outlet assemblies, superficial coatings on the outlet assembly protects against the formations of biofilms and/or other membranes or substances which can impair outflow or lead to infection, and control means disposed within the outlet assembly for controlling a flow of aqueous humor through the tube from the anterior chamber of the eyeball to the external surface of the eyeball, the control means further comprising a replaceable filter disposed within the central chamber of the outer member, the filter having a medicinal agent or combination of agents applied thereto for preventing occlusion of the filter or infection by preventing fibrosis, inflammatory membranes, bacterial adhesions and/or biofilms.

DESCRIPTION OF THE DRAWINGS

In the accompanying drawings which form a part of this specification and are to be read in conjunction therewith and in which like reference numerals are used to indicate like parts in the various views.

DESCRIPTION OF THE PREFERRED EMBODIMENTS

Figure 1:
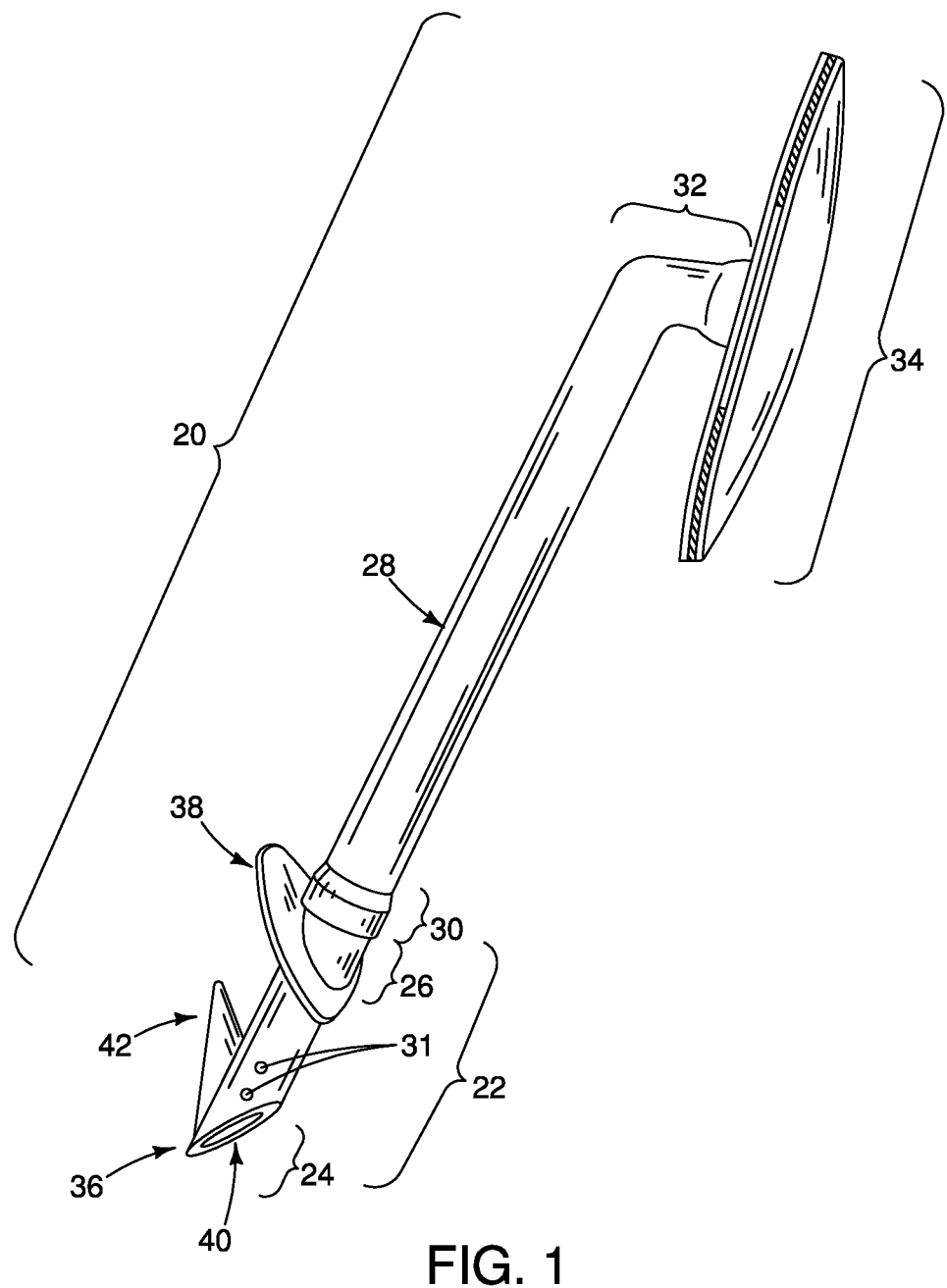
FIG. 1 is a perspective view of a preferred embodiment of a drainage apparatus according to the present invention.

Embodiments of the present invention provide a method and apparatus to direct aqueous humor from the anterior chamber of an eyeball to the external surface of the eyeball as a means to predictably regulate intraocular pressure and treat glaucoma. Importantly, this method eliminates the possibility of failure associated with wound healing. An embodiment of a drainage apparatus 20 according to the present invention is illustrated in FIG. 1. As shown in FIG. 1, the drainage apparatus 20 includes an inlet assembly 22 having a first end 24 and a second end 26, a tube 28 capable of conducting aqueous humor having a first end 30 having drainage holes 31 to prevent clogging and a second end 32, and an outlet assembly 34.

The inlet assembly 22 further includes a beveled tip 36 formed at the first end 24 of the inlet assembly 22, and an insertion plate 38 formed near the second end 26 of the inlet assembly 22. An opening 40 is formed through the inlet assembly 22 allowing aqueous humor to flow through an inner lumen of the inlet assembly 22. An anchor 42 may also be formed near the first end 24 of the inlet assembly 22. Openings 30 provide alternate routes for aqueous humor ingress to inflow drainage apparatus 20 and will reduce the possibility of occlusion at opening 40.

The second end 26 of the inlet assembly 22 is connected to the first end 30 of the tube 28. The inlet assembly 22 and the tube 28 can be manufactured as one unit of the same materials or separately and adhered together. The tube 28 is capable of conducting aqueous humor through its inner lumen. The second end 32 of the tube 28 is connected to the outlet assembly 34.

Figure 2:
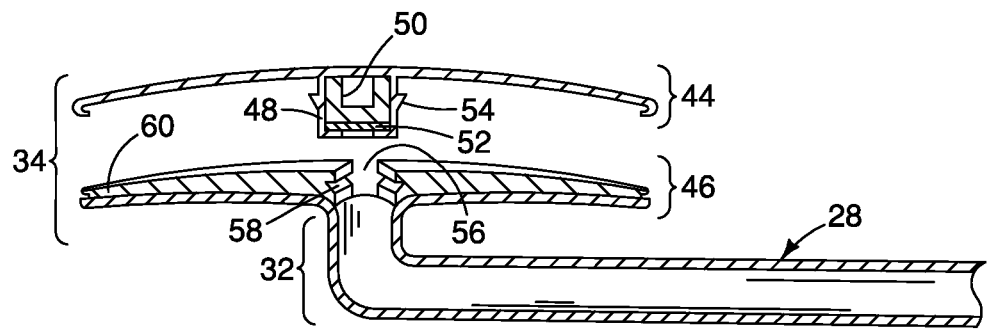
FIG. 2 is a cross-sectional view of the outlet assembly of the preferred embodiment of the drainage apparatus and filter with the outer member removed.
Figure 3:
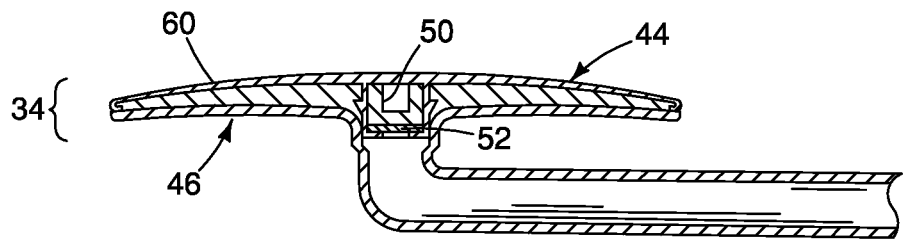
FIG. 3 is another cross-sectional view of the outlet assembly of the drainage apparatus and filter with the outer member attached to the inner member.

As shown in FIGS. 2 and 3, the outlet assembly 34 includes an outer member 44 and an inner member 46. The outer member 44 further includes a central chamber 48 having at least one aperture 50, a filter 52 and a flange 54 disposed along the outer aspect of the central chamber. The inner member 46 includes a central cavity 56, a groove 58 formed therein, and a plurality of spacers 60.

Figure 17:
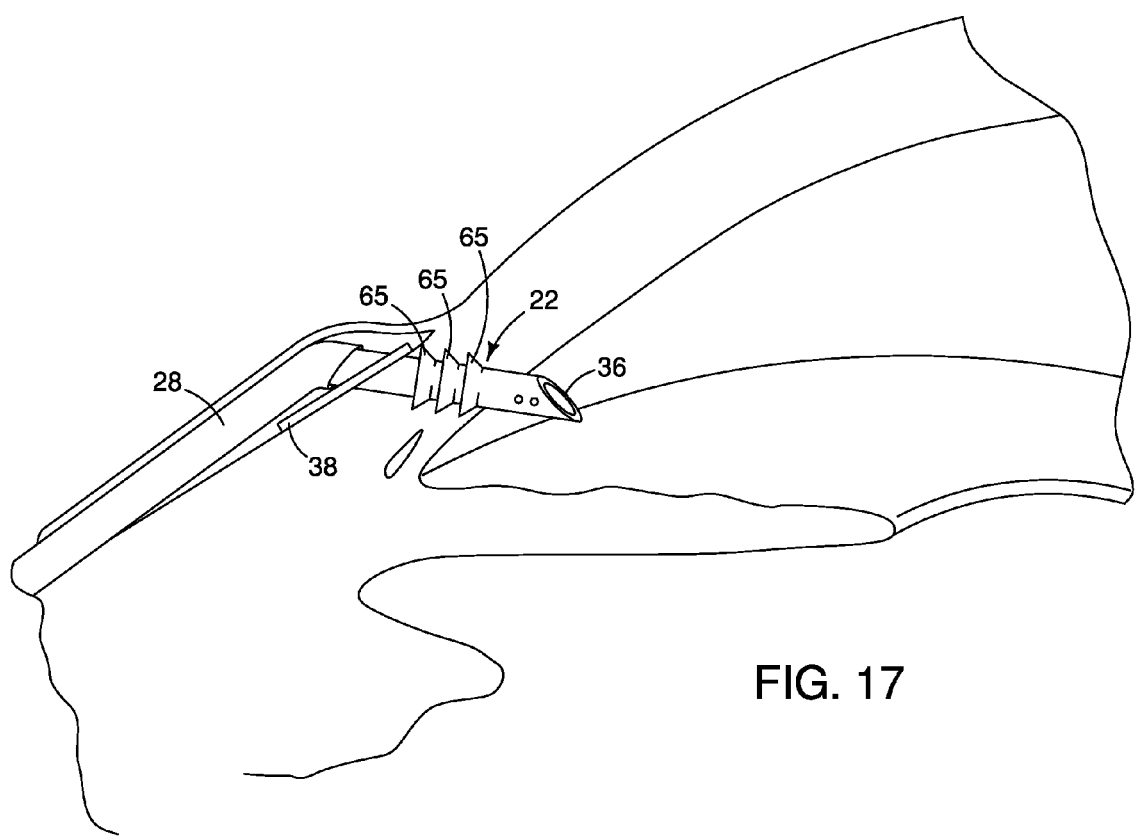
FIG. 17 is a cross-sectional view of an alternative preferred embodiment of the drainage apparatus at a point of insertion into a limbus.
Figure 18:
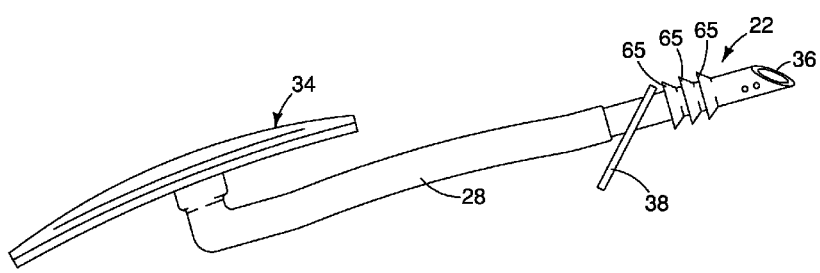
FIG. 18 is a side perspective view of the alternative preferred embodiment of the drainage apparatus illustrated in FIG. 17.
Figure 19:
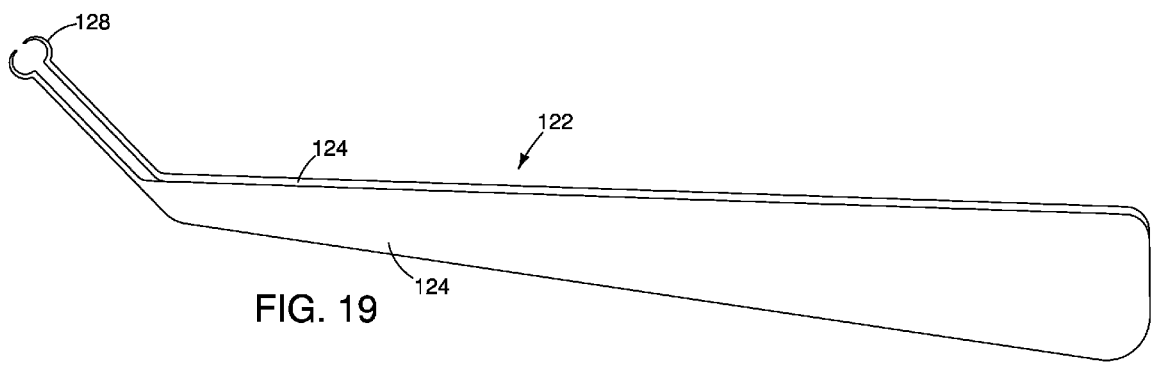
FIG. 19 is a side perspective view of an alternative preferred embodiment of a grasping apparatus for use with one or more preferred embodiments of the drainage apparatus illustrated in FIGS. 1 and 17.

As shown in FIG. 1, the shape of the beveled tip 36 of the inlet assembly 22 allows the first end 24 and opening 40 of the inlet assembly 22 to be more easily inserted into the anterior chamber 62 of an eyeball 64 during the process of inserting the drainage apparatus 20 into the eyeball described in detail below. An anchor 42 may be disposed on the outer aspect near the first end 24 of the inlet assembly 22. In this position, the anchor 42 will help to secure the beveled tip 36 of the first end 24 of the inlet assembly 22 within the anterior chamber 62 of the eyeball 64. Alternatively, as illustrated in FIGS. 17 and 18 a plurality of anchors 65 may be formed on the outer aspect of the first end 24 of the inlet assembly 22, thereby allowing the first end of the inlet assembly 22 to be secured at a number of different lengths within the anterior chamber 62 as may be necessary in certain afflicted eyeballs. The plurality of anchors 65 also enables adequate fixation of the device in eyes with unusual thickness of limbal tissue 104.

In the preferred embodiment shown in FIGS. 1-4, inlet assembly 22 and tube 28 are formed as one unit. In other embodiments, inlet assembly 22 and tube 28 may be formed separately from the same or different materials. When formed separately, the second end 26 of the inlet assembly 22 is attached to the first end 30 of the tube 28. The tube 28 may be formed such that the inner diameter of the first end 30 of the tube is slightly smaller than the outer diameter of the second end 26 of the inlet assembly 22. This allows the second end 26 of the inlet assembly 22 to be inserted into the first end 30 of the tube 28, so that the second end 26 of the inlet assembly and the first end of the tube are held together by a frictional fit. Other known methods of attaching the first end 30 of the tube 28 to the second end 26 of the inlet assembly 22 may also be employed for this purpose, such as welding or the use of adhesive material.

Figure 20:
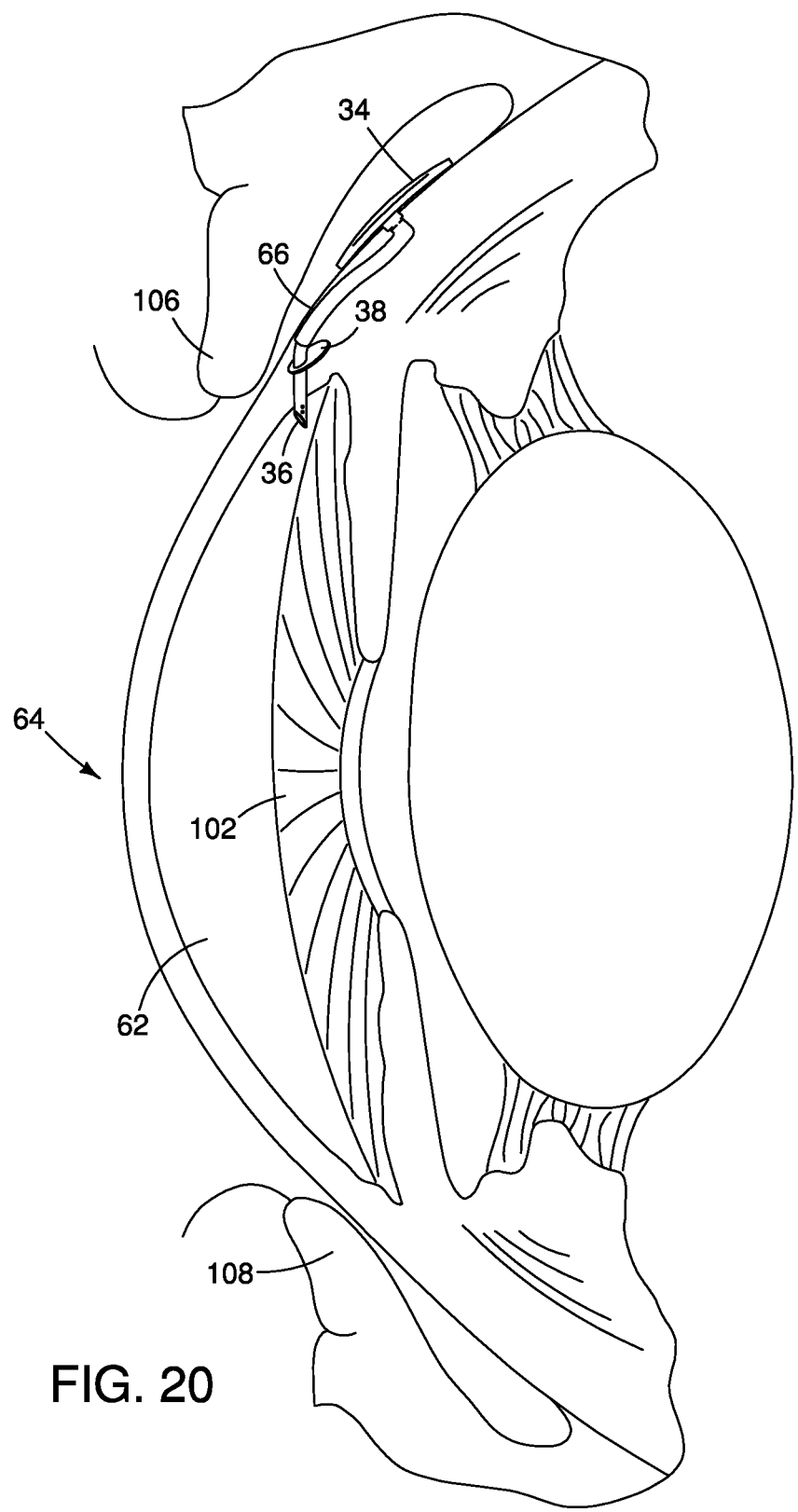
FIG. 20 is a cross-sectional view of an eyeball having the drainage apparatus illustrated in FIGS. 1-4 coupled thereto.

As shown in FIGS. 2, 3 and 20, both the outer member 44 and inner member 46 of the outlet assembly 34 are preferably round and convex in shape, similar to a contact lens, thereby allowing the outlet assembly of the drainage apparatus 20 to sit comfortably on the external surface of the conjunctival layer 66 of the eyeball 64 after insertion. While this particular shape is preferable because it helps provide comfort to the patient, other shapes and sizes for both the outer member 44 and inner member 46 may also be used with the drainage apparatus 20.

The second end 32 of the tube 28 is connected to the inner member 46 of the outlet assembly 34. The tube 28 and the inner member 46 may be formed as a single unit and may be composed of the same material. Alternatively, the tube 28 and the inner member 46 may be formed separately and secured to each other by a frictional fit as described above or through other methods suitable for this purpose.

Figure 4:
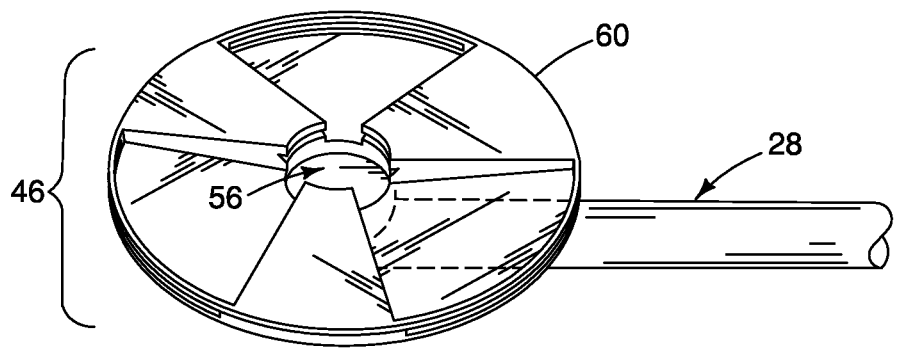
FIG. 4 is a perspective view of the outlet assembly of the preferred embodiment of the drainage apparatus, parts broken away to reveal details of construction.

As shown in FIGS. 2, 3 and 4, a central cavity 56 is formed in the center of the inner member 46. The central chamber 48 of the outer member 44 is received within the central cavity 56. The groove 58 formed within the central cavity 56 serves to receive the flange 54 disposed along the outer aspect of the central chamber 48, thereby securing the central chamber within the central cavity. This also serves to secure the outer member 44 to the inner member 46. As shown in FIG. 3, the central chamber 48 may also extend slightly into the tube 28, further helping to secure the outer member 44 to the inner member 46 by a frictional fit between the tube 28 and the central chamber 48. A gap between the outer member 44 and inner member 46 is maintained by the plurality of spacers 60 formed in the inner member 46. FIG. 4 illustrates one embodiment of the spacers 60 within the inner member 46.

The central chamber 48 of the outer member 44 contains a micropore filter 52. As shown in FIG. 3, when the outer member 44 is secured to the inner member 46, the filter 52 is positioned adjacent to the second end 32 of the tube 28. Aqueous humor flowing from the tube 28 into the outlet assembly 34 is thereby directed through the filter 52. The filter provides resistance to the flow of aqueous humor from the tube 28 into the outlet assembly 34. A filter with smaller pore size, lower pore density, thicker or/and smaller surface area will result in increased flow resistance, thereby decreasing the flow of aqueous humor through the drainage apparatus 20 and providing for a higher intraocular pressure. A filter with larger pore size, higher pore density, thinner and/or larger surface area will result in decreased flow resistance, thereby increasing the flow of aqueous humor through the drainage apparatus 20 and providing for a lower intraocular pressure. In addition, the filter 52 with a pore size smaller than that of bacteria serves as a barrier to microbial infection.

After passing through the filter, the aqueous humor flows out of the central chamber 48 though the apertures 50. The aqueous humor then flows between the spacers 60 into the gap between the outer member 44 and inner member 46. Other openings anywhere along outer member 44 or inner member 48 also can provide possible sites for aqueous flow to the external surface. The aqueous humor then drains out of the outlet assembly 34 onto the external surface of the conjunctival layer 66 of the eyeball 64.

Figure 11:
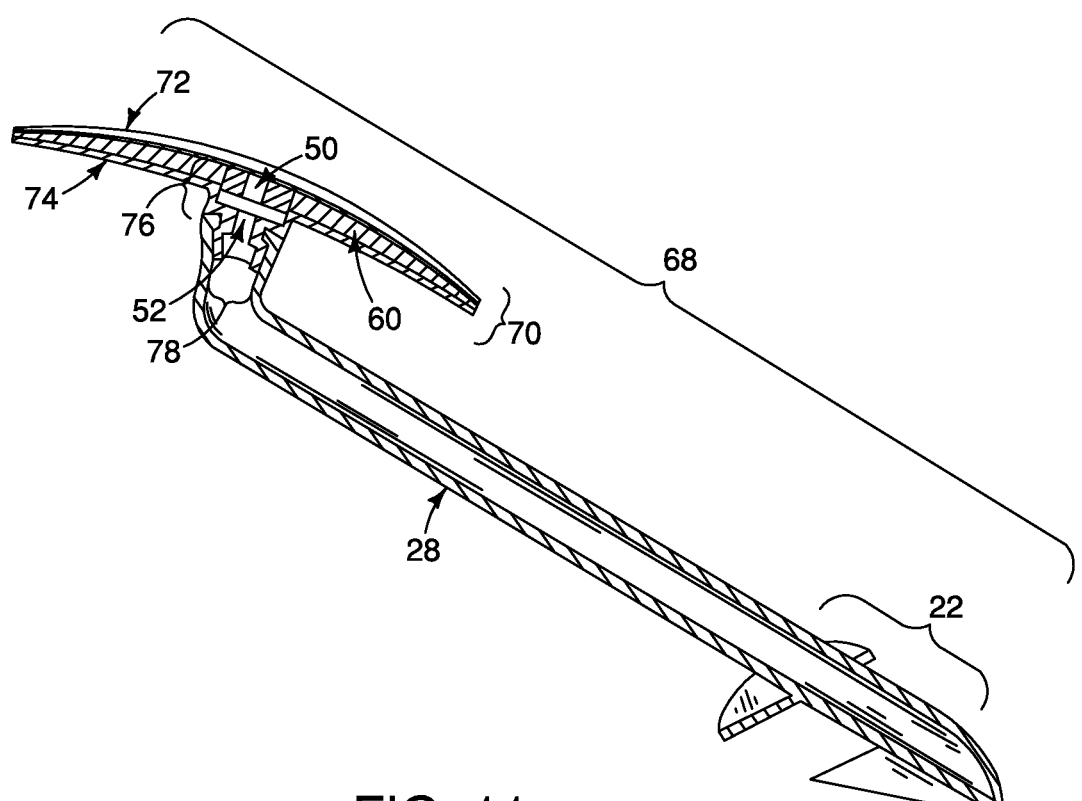
FIG. 11 is a cross-sectional view of another embodiment of the drainage apparatus, in which entire outlet assembly can be replaced.

Another embodiment of the present invention is illustrated in FIG. 11 and provides for a drainage apparatus 68 incorporating a one-piece outlet assembly 70 with the same inlet assembly 22 and tube 28 configuration as drainage apparatus 20. The one-piece outlet assembly 70 includes a first member 72 and a second member 74 which are affixed to each other by means of a chamber 76 and spacers 60. The chamber 76 houses a filter 52 and also contains apertures 50 through which aqueous humor can flow to exit the chamber. A plurality of spacers 60 are disposed between the first member 72 and the second member 74, and serve to maintain a gap between the two so as to allow aqueous humor to flow out of the one-piece outlet assembly 70 onto the external surface of the conjunctival layer 66 of the eyeball 64. Other openings anywhere along first member 72 or second member 74 also can provide possible sites for aqueous flow to the external surface. Both the first member 72 and second member 74 are optimally round and convex in shape, similar to a contact lens, so as to comfortably fit the external curvature of the eyeball 64. While this shape is beneficial and helps provide comfort to the patient, other shapes and sizes for both the first member 72 and second member 74 may also be used with the one-piece outlet assembly 70.

A coupling mechanism 78 is formed on the second member 74 and serves to attach the second end 32 of the tube 28 to the one-piece outlet assembly 70. The coupling mechanism 78 is received within the second end 32 of the tube 28 and is held therein by a frictional fit. The coupling mechanism is hollow, thereby allowing aqueous humor to flow through its inner lumen. The filter 52 is disposed between the coupling mechanism 78 and the apertures 50 within the central chamber 76. The filter provides resistance to the flow of aqueous humor from the tube 28 into the one-piece outlet assembly 70 as described above.

Aqueous humor flows from the tube 28 through the coupling mechanism 78 and is directed through the filter 52. After passing through the filter 52, the aqueous humor flows through the apertures 50 of the chamber 76, into the area between the spacers 60. The aqueous humor then exits the one-piece outlet assembly 70 by flowing through the gap between the first member 72 and second member 74 or though openings on the inner or outer surface of outlet assembly 70, thereby draining onto the external surface of the conjunctival layer 66 of the eyeball 64.

Figure 6:
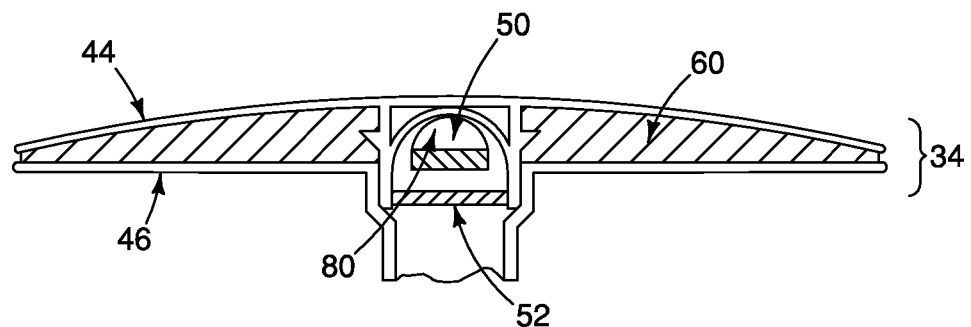
FIG. 6 is a cross-sectional view of the outlet assembly of the drainage apparatus shown in FIGS. 1-4 including an optional valve.

As illustrated in FIG. 6, a valve 80 may also be employed to provide resistance to the flow of aqueous humor through drainage apparatus 20 or 68. When a valve 80 is employed in drainage apparatus 20 or 68, a filter 52 is still required to prevent the ingress of microorganisms, but the filter itself does not provide sufficient resistance to the outflow of aqueous humor from the eyeball 64 to influence the intraocular pressure. The valve 80 is ideally pressure sensitive and unidirectional, and may include a thin membrane of silicone or similar material. The valve 80 is positioned between the filter 52 and the apertures 50 within either the central chamber 48 of the outlet assembly 34 or the chamber 76 of the one-piece outlet assembly 70. In this position, aqueous humor initially flows through the filter 52 before reaching the valve 80. A sufficient amount of intraocular pressure exerted on valve 80 will cause valve 80 to deform, allowing aqueous humor to flow into the outlet assembly 34 or one-piece outlet assembly 70 and on to the surface of the eyeball 64. Valves of different levels of intraocular pressure resistance may be utilized within drainage apparatus 20 or 68 depending on the desired postoperative level of intraocular pressure within the eyeball 64.

Drainage apparatus 20 and 68 function to drain aqueous humor from the anterior chamber of the eyeball 64 to the external surface of the eyeball. Drainage apparatus 20 or 68 is inserted in the eyeball 64 such that the first end 24 of the inlet assembly 22 is held within the anterior chamber 62 of the eyeball 64, the tube 28 lies subconjunctivally, conforming to the external curvature of the eyeball, and the outlet assembly 34 or one-piece outlet assembly 70 is positioned above the external surface of the eyeball. Aqueous humor from the anterior chamber 62 of the eyeball 64 enters the opening 40 of the first end 24 of the inlet assembly 22. The aqueous humor flows through the inlet assembly 22 and into the tube 28 which lies underneath the conjunctiva 66 and pericardial patch 100. The tube 28 conducts the aqueous humor into the outlet assembly 34 or one-piece outlet assembly 70. As the aqueous humor flows into the outlet assembly 34 or one-piece outlet assembly 70, the aqueous humor passes through a filter 52 and perhaps also through a valve 80, 151, or 158. The filter functions to provide resistance to the flow of aqueous humor when used alone. If coupled with a valve, the valve instead provides this resistance by having an opening and closing pressure. After flowing through the filter 52 with or without valve 80, 151, or 158, the aqueous humor flows through the outlet assembly 34 or one-piece outlet assembly 70 and drains onto the exterior surface of the eyeball 64.

Figure 8:
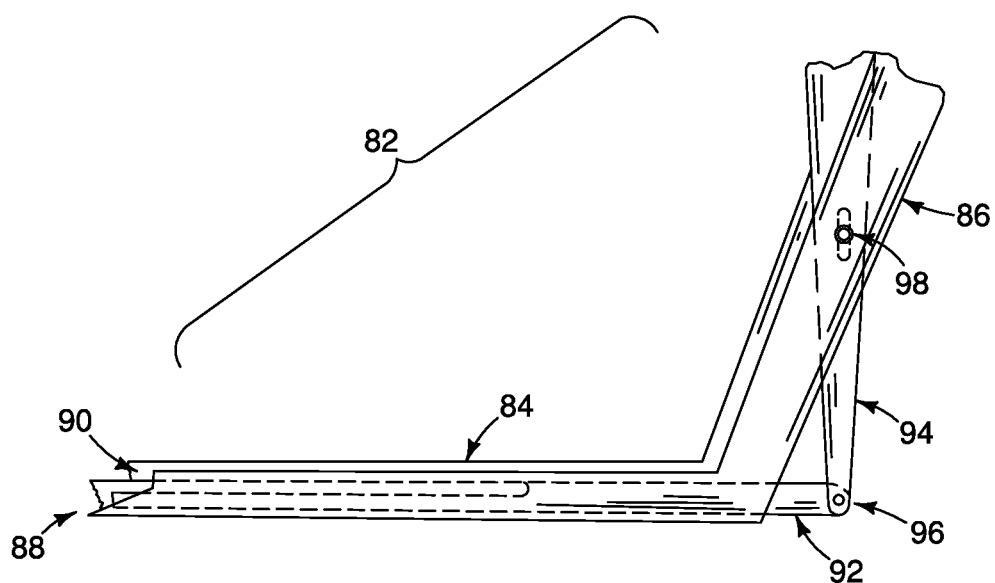
FIG. 8 is a perspective view of a device to insert a drainage apparatus into an eyeball.

The present invention also discloses an apparatus and method for inserting drainage apparatus 20 or 68 into the eyeball 64. FIG. 8 illustrates an inserting apparatus 82 which can be used to insert either embodiment of drainage apparatus 20 or 68 into the eyeball 64. The inserting apparatus 82 is designed to greatly simplify insertion of drainage apparatus 20 or 68 into the eyeball 64 so as to minimize the duration and invasiveness of the insertion procedure.

Figure 9:
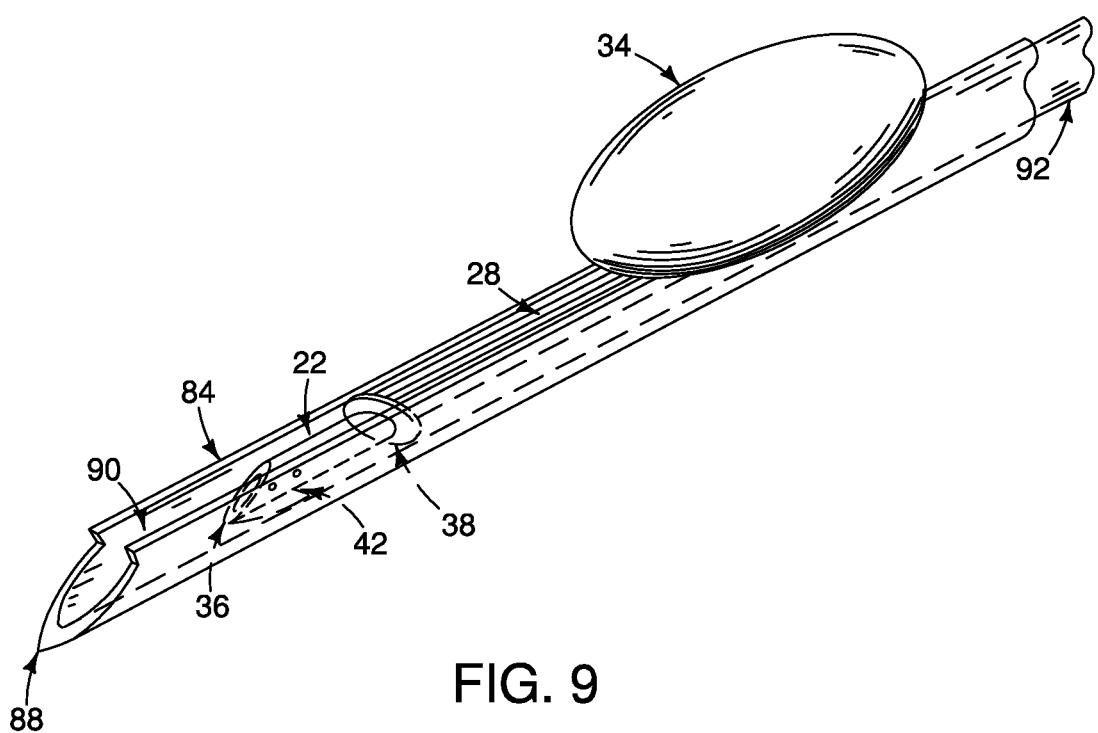
FIG. 9 is a perspective view of the drainage apparatus seated in the device to insert the drainage apparatus into an eyeball.

As shown in FIGS. 8 and 9, the inserting apparatus 82 includes an insertion prong 84 attached to a first handle 86. The insertion prong 84 has an insertion point 88. The insertion prong 84 also defines an aperture 90 wherein a second prong 92 is slideably received. As shown in FIG. 9, both the insertion prong 84 and the second prong 92 have an opening formed in their upper surface allowing for drainage apparatus 20 or 68 to be received and seated prior to insertion into the eyeball 64. The second prong 92 is attached to a second handle 94 by means of a first hinge 96. The second handle 94 is attached to the first handle 86 by means of a second hinge 98. When the first handle 86 is held in place, the second handle 94 is pushed towards the first handle 86, causing a rotation at the second hinge 98 such that the second handle 94 will push the second prong 92 toward the insertion point 88. Additionally, the second prong 92 and the insertion prong 84 can be made as long parallel pieces without a bend, hinge 96, and second hinge 98 (not shown). In this embodiment, the second prong 92 advances forward within insertion prong 84 by manually or electronically pushing on second prong 92.

Figure 10:
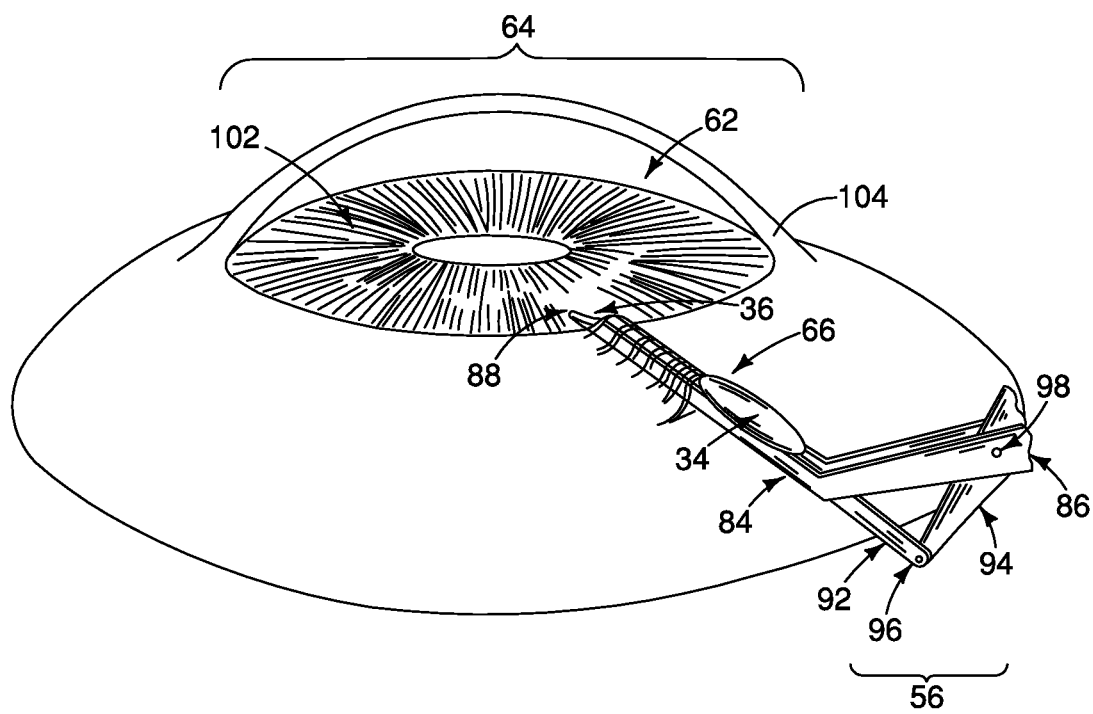
FIG. 10 is a perspective view of a device for inserting a drainage apparatus into an eyeball, a drainage apparatus, and an eyeball at the point of insertion into the eyeball.
Figure 14:
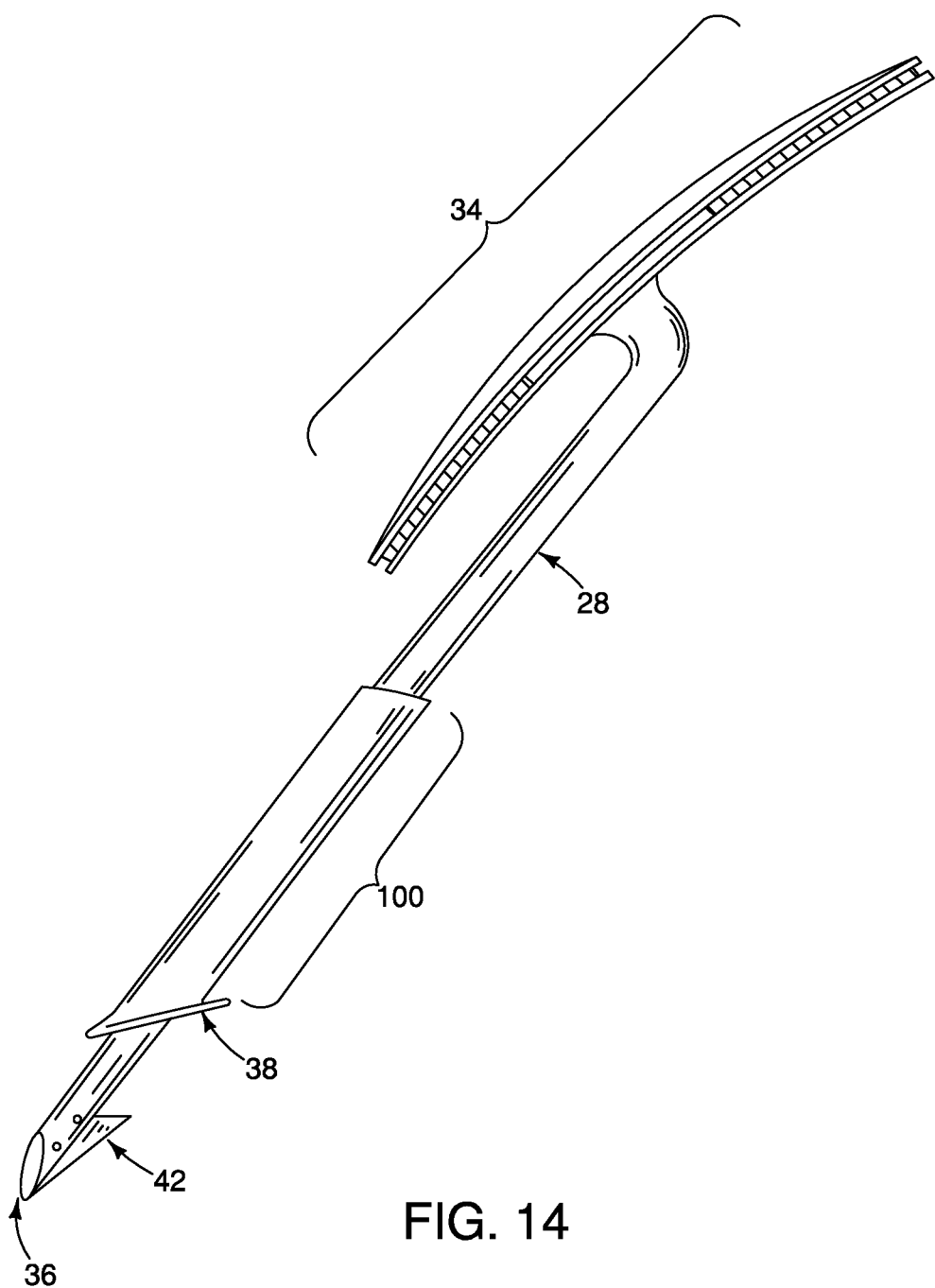
FIG. 14 is a perspective view of the drainage apparatus with a pericardial patch secured to the tube and insertion plate of the apparatus.
Figure 16:
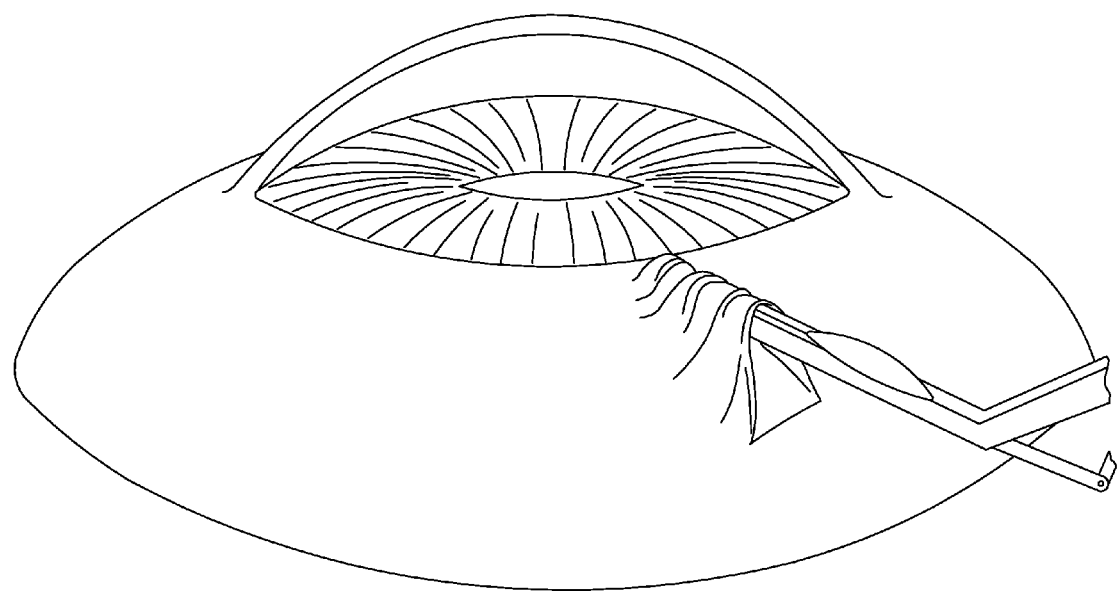
FIG. 16 is a perspective view of the device illustrated in FIG. 8 coupled to a drainage apparatus at a point of insertion into an eyeball at a preferred angle of insertion.

The process of inserting drainage apparatus 20 or 68 into the eyeball 64 with the inserting apparatus 82 is illustrated in FIG. 10. As shown in FIG. 14, a pericardial patch 100 is secured via suturing, tissue adhesive (glue) or other commonly known means around the tube 28 and insertion plate 38 of drainage apparatus 20 or 68 prior to insertion. In addition to pericardium, patches may be fashioned of sclera, dura mater, fascia lata, or similar material. Drainage apparatus 20 or 68 is then seated within the inserting apparatus 82 such that the beveled tip 36 of the inlet assembly 22 is oriented towards the insertion point 88 of the insertion prong 84. As shown in FIG. 9, the outlet assembly 34 or one-piece outlet assembly 70 is seated along the upper external aspect of the insertion prong 84. The distal end of the second prong 92 is positioned adjacent to the posterior aspect of the insertion plate 38. FIG. 10 illustrates the position of the inserting apparatus 82 and drainage apparatus 20 or 68 at insertion into the eyeball 64, the eyeball having an iris 102, an anterior chamber 62, a conjunctival layer 66 and a limbus 104. An incision is initially made in the conjunctival layer 66. The insertion point 88 of the insertion prong 84 and the second prong 92 are guided through this incision and pushed beneath the conjunctival layer 66 to the point at which the insertion point 88 and the beveled tip 36 of the inlet assembly 22 reaches the external boundary of the limbus 104. The insertion point 88 of the insertion prong 84 may also be driven through the conjunctival layer 66 without an initial incision. In some eyeballs 64 with scarring between the conjunctival layer 66 and the underlying episcleral surface, blunt-tipped scissors can be inserted through the conjunctival incision to bluntly spread tissues to form a space between the conjunctival layer 66 and the episcleral surface. Alternatively, fluid (such a balanced salt solution) or a viscoelastic substance can be injected into this space to separate the conjunctival layer 66 from the episcleral surface. When properly aligned at limbus 104 with the insertion prong 84 and the second prong 92 positioned parallel to the plane of the iris by raising the end of the insertion device opposite the insertion point 88 as depicted in FIG. 16, the insertion point 88 is driven through the limbal tissue into the anterior chamber 62. Prior to driving insertion point 88 into the anterior chamber 62, viscoelastic material, if needed, can be injected into the anterior chamber through a separate stab incision through the peripheral cornea. After the insertion point 88 enters the anterior chamber 62, the second handle 94 is drawn towards the first handle 86, causing the second prong 92 to push against the posterior aspect of the insertion plate 38 and drive the beveled tip 36 of the inlet assembly 22 through the limbus 104 into the anterior chamber. The opening 40 of the inlet assembly 22 may then be secured in place within the anterior chamber 62 by the anchor 42, which rests against the angle or corneal endothelium in the anterior chamber 62. In addition, the insertion plate 38 rests against the external surface of the limbus 104 underneath the conjunctival layer 66 and also functions to hold the inlet assembly 22 in proper position. As illustrated in FIGS. 17 and 18, a plurality of the anchor flanges 65 may also be formed upon the inlet assembly 22 to accommodate varying limbal thicknesses. Alternatively, the distance between anchor 42 and insertion plate 38 can be varied allowing the surgeon to choose the appropriate inlet assembly 22 according to the limbal thickness.

Figure 5:
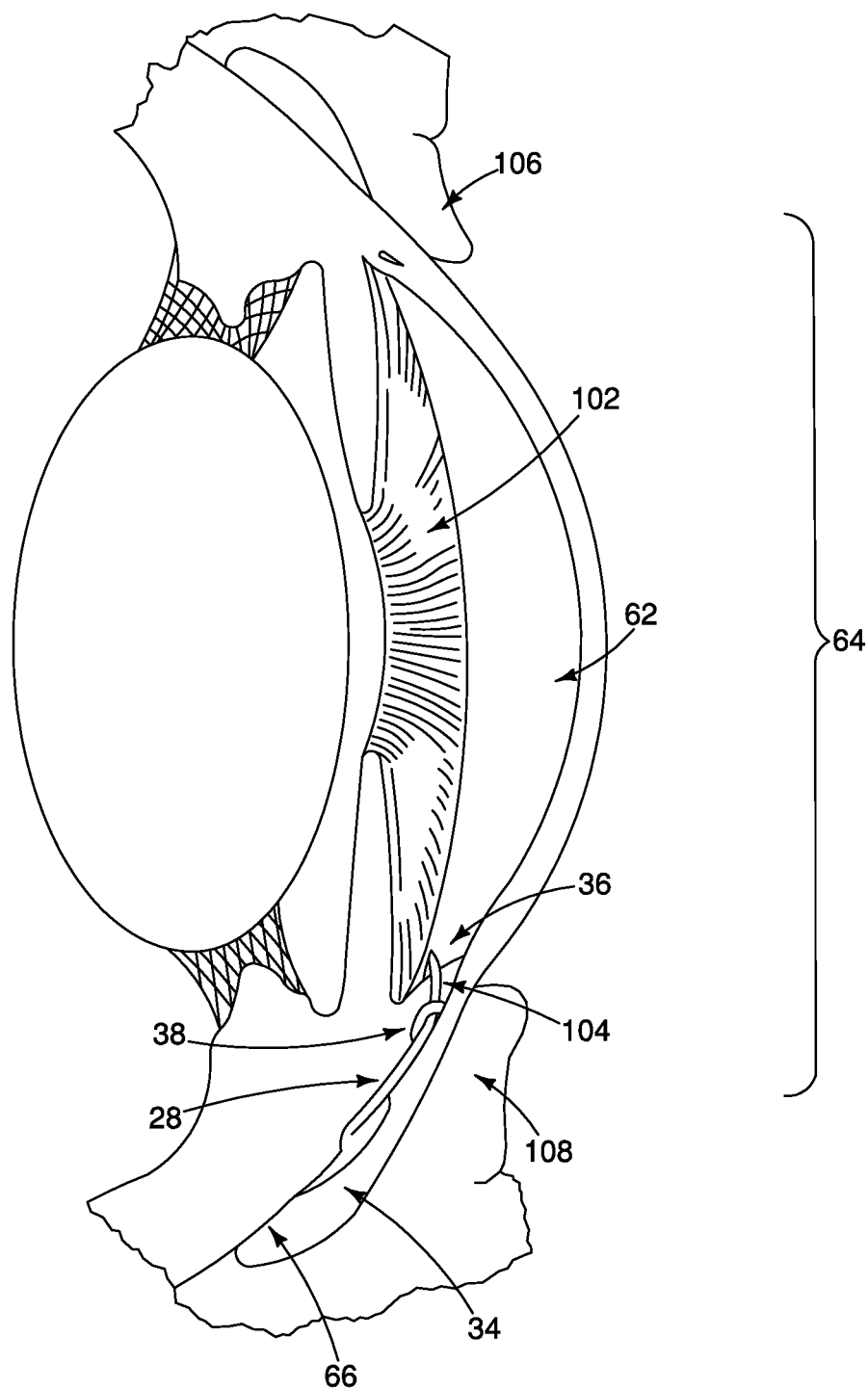
FIG. 5 is a cross-sectional view of an eyeball showing the drainage apparatus inserted therein.
Figure 12:
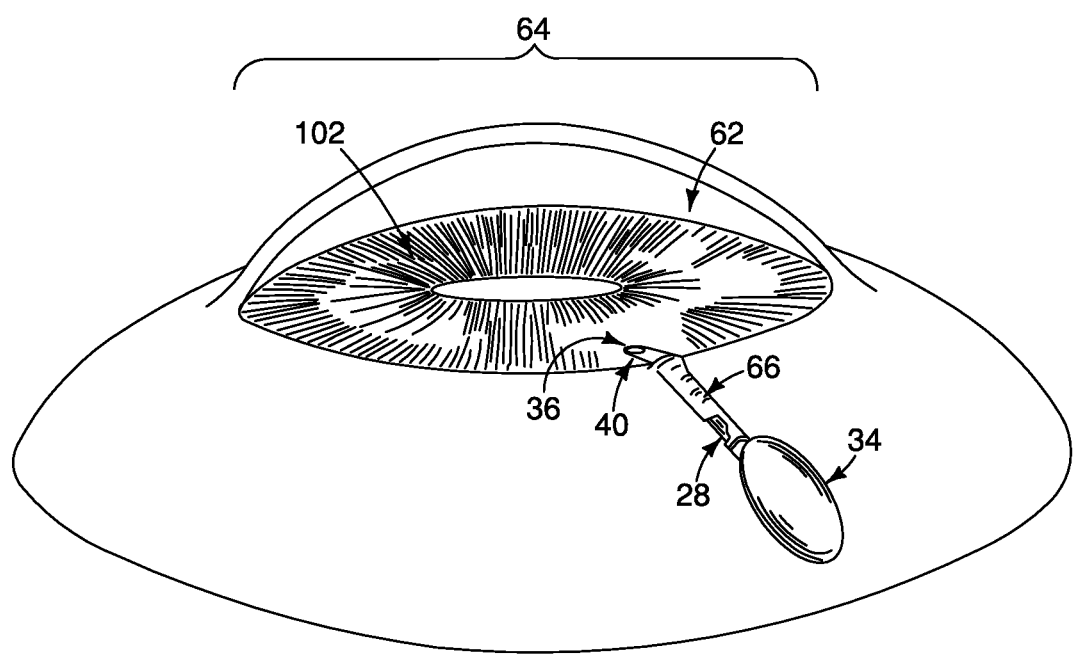
FIG. 12 is a perspective view of an eyeball into which a drainage apparatus has been inserted.

Once the inlet assembly 22 has been properly positioned, the inserting apparatus 82 is removed, leaving the drainage apparatus 20 or 68 in place as shown in FIG. 12. As illustrated in FIG. 12, once in position, the tube 28 lies comfortably on the episcleral surface, and conforms to the curvature of the eyeball 64. In this position, the conjunctival layer 66 covers the pericardial patch 100 and tube 28. The pericardial patch 100 attached to the insertion plate 38 serves to protect the conjunctival layer 66 from eventual erosion caused by the tube 28 or the insertion plate 38. As shown in both FIG. 12 and FIG. 5, the outlet assembly 34 is ideally situated along the external ocular surface of the eyeball 64 in the conjunctival cul-de-sac, between the eyeball 64 and the upper eyelid 106 or lower eyelid 108. When inserted in this fashion, aqueous humor is directed from the anterior chamber 62 of the eyeball 64 to the tear film surface of the eyeball.

If it is necessary to secure and stabilize the outlet assembly 34 or the one-piece outlet assembly 70, a suture can be used to fix it to the underlying conjunctival layer 66. This suture can be passed through the periphery of the outlet assembly 34 or the one-piece outlet assembly 70 and through the conjunctival layer 66 only, or through both the conjunctival layer and episcleral tissue. Alternatively, fixation of the outlet assembly 34 or the one-piece outlet assembly 70 can be accomplished with tissue glue. Another means of fixation would be to coat the inner aspect of the inner member 46 of the outlet assembly 34 or the inner aspect of the second member 74 of the one-piece outlet assembly 70 with hydroxyapatite or similar material. If the epithelium of the conjunctival layer 66 underlying the outlet assembly 34 or the one-piece outlet assembly 70 is abraded, the conjunctiva will adhere to the hydroxyapatite on the inner aspect of either the inner member 46 or the second member 74.

Figure 15:
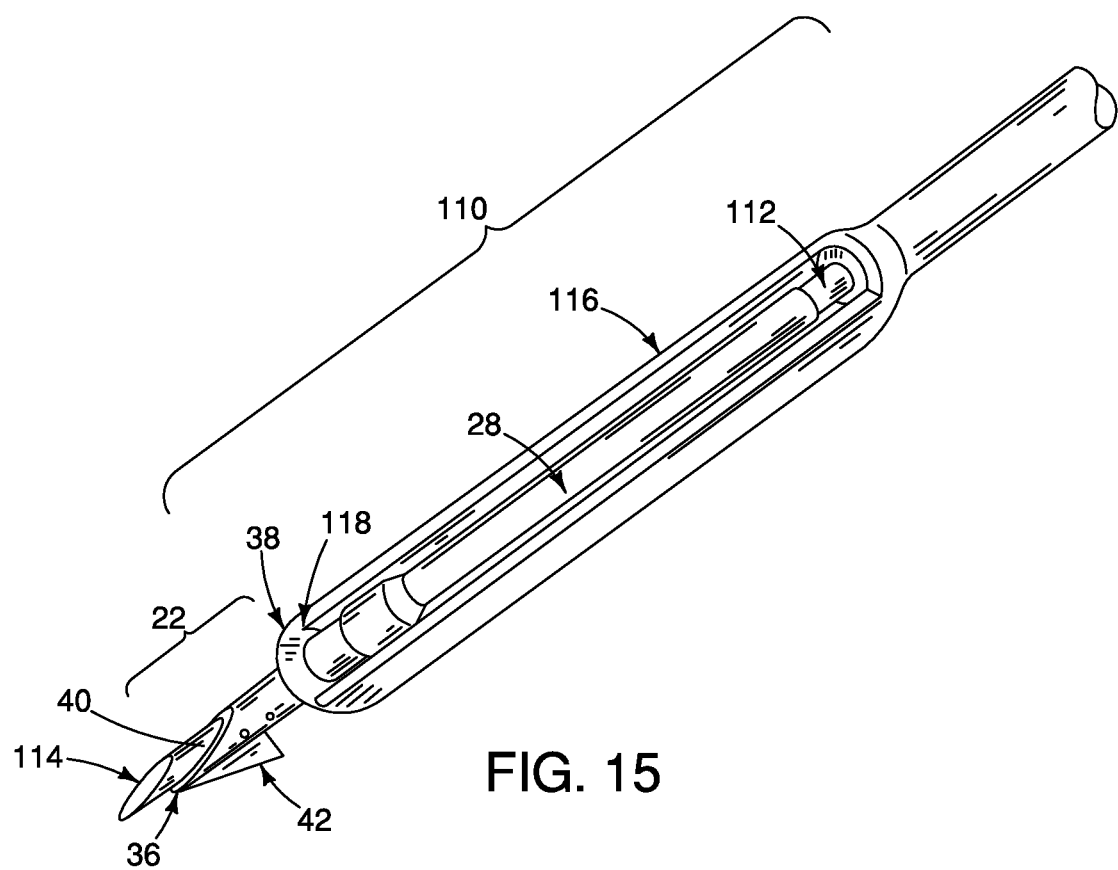
FIG. 15 is a perspective view of an alternative embodiment of a device for inserting a drainage apparatus into an eyeball, parts broken away to reveal details of construction and operation.

Another embodiment of the inserting apparatus 110 is illustrated in FIG. 15. The inserting apparatus 110 is designed to be used specifically for insertion of drainage apparatus 68, but also can be used with drainage apparatus 20. This embodiment is used to insert the inlet apparatus 22 and tube 28 of drainage apparatus 68 into the eyeball 64, allowing the one-piece outlet assembly 70 to be attached to the second end 32 of the tube 28 after insertion. When used to insert drainage apparatus 20, outlet assembly 34 should be removed, but is replaced after the insertion the inlet assembly 22 and tube 28.

As shown in FIG. 15, the inserting apparatus 110 includes a trocar 112 having an incision end 114 and secured within an outer cylinder 116 at its opposite end. The outer diameter of the trocar 112 is slightly smaller than the inner diameter of the tube 28. The outer cylinder 116 has an open end 118 beyond which the incision end 114 of the trocar 112 extends. The outer cylinder 116 has an inner diameter slightly larger than the outer diameter of the tube 28. A pericardial patch 100 is secured around the tube 28 and the insertion plate 38 as described earlier. The tube 28 and inlet assembly 22 are then inserted over the trocar 112 within the outer cylinder 116 by inserting the incision end 114 through the second end 32 of the tube so that the incision end passes through the tube and protrudes slightly beyond the opening 40 of the inlet assembly. In this position, the incision end 114 is situated in line with the beveled tip 36 of the inlet assembly 22 and the inlet assembly protrudes beyond the distal end of the outer cylinder 116 but still surrounds the incision end of the trocar 112. The insertion plate 38 is positioned against the open end 118 of the outer cylinder 116.

An incision is first made in the conjunctival layer 66 with either a scissors or with the incision end 114 of the trocar 112, and the inlet assembly 22, tube 28, outer cylinder 116 and trocar are then guided through this incision and pushed beneath the conjunctival layer 66 to the point at which the incision end of the trocar reaches the external boundary of the limbus 104. In certain eyeballs, the conjunctival layer 66 may need to be separated from the underlying episcleral tissue with blunt dissection, fluid, or viscoelastic material as previously described. At this point, the outer cylinder 116 and trocar 112 are pushed forward with an orientation parallel to the plane of the iris, causing the incision end 114 of the trocar to pierce through the limbus 104. This also causes the outer cylinder 116 to press against the insertion plate 38 and drive the beveled tip 36 of the inlet assembly 22 through the limbus 104 into the anterior chamber 62. The opening 40 of the inlet assembly 22 may then be secured in place within the anterior chamber 62 as previously described. The outer cylinder 116 and trocar 112 are then removed, and the tube 28 remains in position subconjunctivally as previously described.

The second end 32 of the tube 28 exits through the initial incision of the conjunctival layer 66 several millimeters posterior from the limbus 104. The one-piece outlet assembly 70 is then attached to the second end 32 of the tube 28 by attaching a plunger or similar suctioning device (of the type which is shown at 54 in FIG. 7) to the external surface of the first member 72. The coupling mechanism 78 of the one-piece outlet assembly 70 is then guided into position over the second end 32 of the tube 28. Once in place, manual pressure is applied to seat the coupling mechanism 78 into the second end 32 of the tube 28. The one-piece outlet assembly 70 lies in the same position as the outlet assembly 34 in FIGS. 5 and 12, along the external ocular surface of the eyeball 64 in the conjunctival cul-de-sac between the eyeball and the upper eyelid 106 or lower eyelid 108. When inserted in this fashion, aqueous humor is directed from the anterior chamber 62 of the eyeball 64 to the tear film surface of the eyeball.

The present invention also provides for removal and replacement of the filter 52 and/or valve 80 from drainage apparatus 20 or 68. This feature allows for the rate of outflow of aqueous humor from the anterior chamber 62 of the eyeball 64 through drainage apparatus 20 or 68 to be post-surgically adjusted in a predictable manner. In drainage apparatus 20, this process involves removing and replacing the outer member 44 which houses the filter 52 and/or valve 80 in the central chamber 48. In order to remove and replace the outer member 44 and filter 52, the outlet assembly 34 must first be stabilized.

Figure 7:
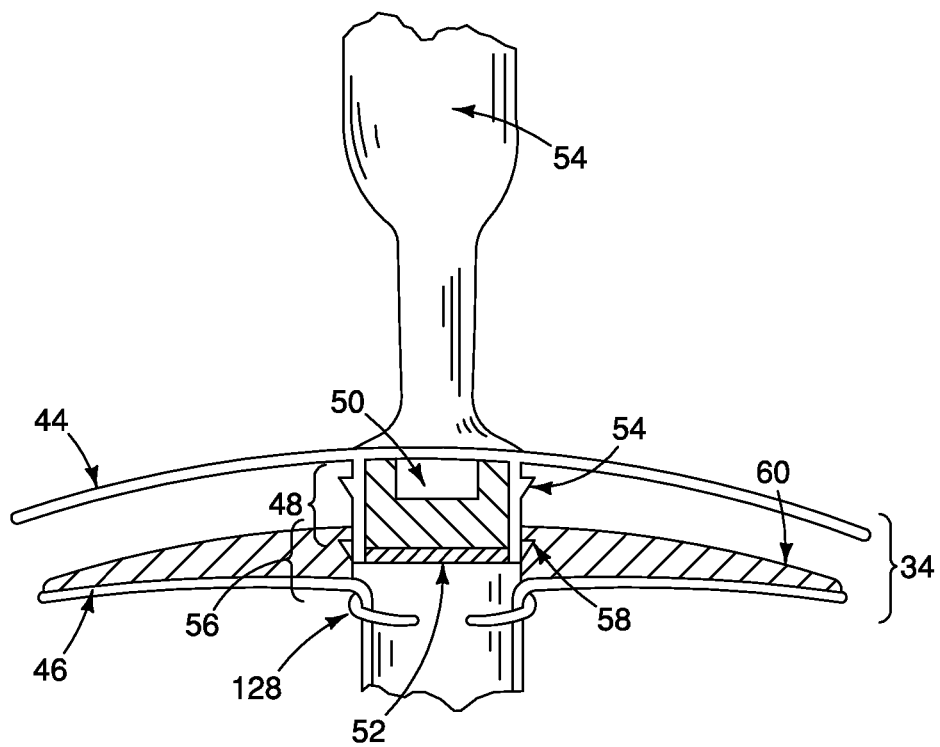
FIG. 7 is a cross-sectional view of the outlet assembly of the drainage apparatus shown in FIGS. 1-4 with a suctioning device attached to the outer member and inserting it upon the inner member during filter exchange.
Figure 13:
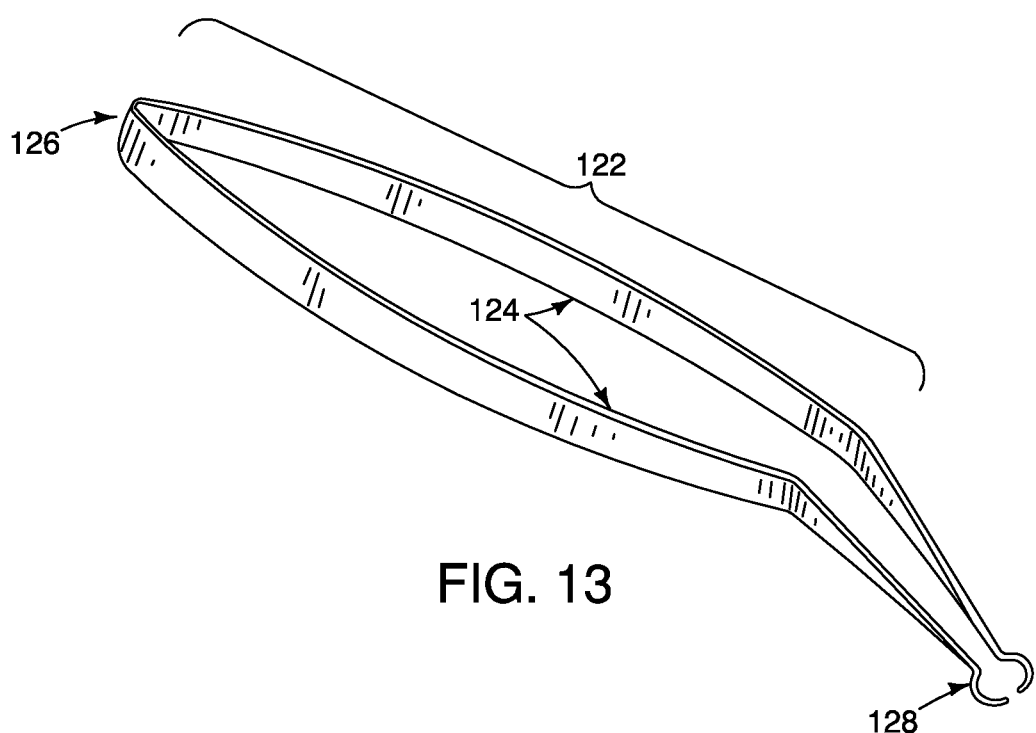
FIG. 13 is a perspective view of a device for stabilizing a drainage apparatus to allow for the removal and replacement of valves or filters within the drainage apparatus.

This is accomplished by use of the grasping apparatus 122 illustrated in FIG. 13. The grasping apparatus 122 includes two elongated members 124, joined at their proximal end 126, which taper to form an opposable grasping structure 128 at their distal end. This opposable grasping structure 128 is shaped to match the external contour of the second end 32 of the tube 28, thereby allowing a user to grasp the second end of the tube so as to secure the outlet assembly 34 as illustrated in FIG. 7. Once the outlet assembly 34 is secured, the outer member 44 may be removed from the inner member 46 by cutting the superficial aspect of the central chamber 48 of the outer member with a scalpel or other surgical cutting tool and removing it from the inner member with a forceps. The flange 54 must also be removed from the groove 58 of the central cavity 56. The design of drainage apparatus 20 allows for the outer member 44 to be easily removed in this manner without damaging the inner member 46. Once the outer member 44 is removed, a new outer member and filter 52 can be attached to the inner member 46. As illustrated in FIG. 7, a plunger or similar suctioning device 54 is attached to the external surface of a replacement for the outer member 44, which allows the outer member to be guided into place by aligning the central chamber 48 of the outer member into the central cavity 56 of the inner member 46. Once in place, manual pressure is applied to seat the flange 54 of the central chamber 48 within the groove 58 of the central cavity 56. Once this attachment is made, the plunger or similar suctioning device 120 is removed from the outer member 44, leaving the outer member in place. Alternate methods for removing and replacing the outer member 44 from the outlet assembly 34 may also be used.

Removal and replacement of the filter 52 and/or valve 80, 151, or 158 in drainage apparatus 68 is accomplished through the removal and replacement of the one-piece outlet assembly 70. The grasping apparatus 122 is used to grasp the second end 32 of the tube 28. Once the second end 32 of the tube 28 is secured, the one-piece outlet assembly 70 may be removed by sectioning it centrally with a scalpel or other surgical cutting device. A forceps may be used to grasp the one-piece outlet assembly 70 either centrally or more peripherally as necessary to help facilitate this process. The method for inserting a replacement one-piece outlet assembly 70 is similar to the procedure described above. A plunger or similar suctioning device 120 is attached to the external surface of the first member 72 of a replacement for the one-piece outlet assembly 70, and the coupling mechanism 78 of the one-piece outlet assembly 70 is guided into position over the second end 32 of the tube 28. Once in place, manual pressure is applied so as to seat coupling mechanism 78 into the second end 32 of the tube 28. The plunger or similar suctioning device 120 is then removed. Alternate methods for removing and replacing the one-piece outlet assembly 70 from drainage apparatus 68 may also be employed.

The method to change filters in drainage apparatus 20 and 68 disclosed herein as a means to predictably control and regulate the level of intraocular pressure in the eyeball 64 without invasive surgery is a novel feature of the present invention. This feature allows one to predictably control the flow of aqueous humor out of the anterior chamber 62 of the eyeball 64 to achieve a predetermined postoperative target intraocular pressure. If the postoperative intraocular pressure is unacceptably high or low, the current filter 52 with or without valve 80, 151, or 158 can be replaced with a filter 52 with or without valve 80, 151, or 158 to increase or decrease the flow of aqueous humor out of the eyeball 64, thus reducing or increasing the intraocular pressure in the eyeball.

The outlet assembly 34 of drainage apparatus 20 is designed so that the implant site, the central cavity 56 and the filter 52 and/or valve 80, 151, or 158 are surrounded by the outer member 44 and inner member 46, and are not directly exposed to the external surface of the eyeball 64. The same is true with drainage apparatus 68, wherein the first member 72 and second member 74 surround the implant site and the filter 52 and/or valve 80, 151, or 158. This feature of drainage apparatus 20 and 68 greatly reduces the possibility of foreign material entering and clogging drainage apparatus 20 or 68, subsequently hindering or negating its function. In addition, a filter 52 with appropriate pore diameter presents an absolute barrier against bacterial infiltration of drainage apparatus 20 or 68, preventing the possibility of an intraocular infection. The present invention may also incorporate a layer of hydroxyapatite or similar material like porous polyethylene and fibronectin around the second end 32 of the tube 28 to stimulate the growth of the surrounding conjunctival layer 66 into the external surface of the tube, thereby providing a barrier around the external aspect of drainage apparatus 20 or 68. The hydroxyapatite also can extend further along the subconjunctival aspect of tube 28 to further secure the device in the proper position.

The use of drainage apparatus 20 and 68, and inserting apparatus 82 and 110 provide tremendous advantages over the prior art. Other drainage devices and surgical techniques designed to decrease intraocular pressure and treat glaucoma are invasive and lengthy procedures, requiring multiple incisions into the eyeball. Patients often face long postoperative recovery periods following such procedures. Other drainage devices in the art are also very difficult to properly insert, and operate to drain aqueous humor into a bleb or fibrous capsule which can scar and cease to function over time requiring additional surgery to correct. Inserting apparatus 82 and 110 provide a greatly simplified procedure for insertion of drainage apparatus 20 and 68, requiring only one incision in the conjunctival layer 66, and in certain instances no incisions at all. Drainage apparatus 20 or 68 also drains aqueous humor out of the eyeball entirely, negating the need for the creation of either a fibrous capsule or a bleb. Since the insertion procedure for the present invention is greatly simplified, the operating and recovery time for the patient is considerably shortened. The insertion procedure for the present invention is far less invasive than other surgical procedures currently used to increase aqueous humor drainage or insert drainage devices. A significant advantage of the present invention compared to commercially available devices is that the outcome of the surgical procedure is reliably predictable because it is independent of the vagaries of wound healing. The possibilities of insufficient wound healing leading to hypotony and extrusion of the device, and excessive healing resulting in failure are eliminated. The intraocular pressure is fully adjustable by changing the filter with or without the valve to achieve the desired result. If the filter becomes occluded, it can be replaced. In addition, the convex lens shape of the outlet assembly 34 and one-piece outlet end 70 makes the use of drainage apparatus 20 or 68 comfortable for the patient.

Optimally, the inlet assembly 22 of the drainage apparatus 20 and 68 is formed from silicone-based material like Silastic®. Alternatively, a hard plastic, such as polymethyl methacrylate (PMMA), pyrolytic carbon (PyC), or acrylic, a durable glass or surgical metal, such as surgical steel, may be required. The material from which the inlet assembly 22 is composed may need to be resilient to facilitate the insertion procedure. A hard, resilient material would enable the inclusion of optional inlet holes 130 distal to the opening 40 in the event that the opening 40 becomes occluded with intraocular tissue. Such holes 130 would also reduce the possibility of the opening 40 becoming occluded during the use of drainage apparatus 20 or 68. However, the design of the insertion point 88 of inserting apparatus 82 is sufficient to pierce the limbus 104 so as to allow the inlet assembly 22 to be properly positioned within the anterior chamber 62, without necessarily requiring a hard material for the inlet assembly. Likewise, the incision end 114 of the trocar 112 of inserting apparatus 110 may negate the need for a hard material for the inlet assembly 22. A softer material for the inlet assembly 22 would reduce the possibility of damage to intraocular tissues such as the cornea, iris or lens.

The tube 28 is optimally formed from a highly durable yet flexible material, such as Silastic® or silicone. The tube 28 must be flexible, but should not be easily ruptured, bent or kinked so as to stop the flow of aqueous humor or hinder the drainage function of the drainage apparatus 20 or 68. The external surface of the tube 28, particularly the area nearest the outlet assembly 34 or 70, is optimally coated with a material such as hydroxyapatite so as to enable the growth of the surrounding conjunctival layer 66 into the external surface of the tube 28, providing an absolute barrier between the outside surface of the tube and the conjunctival layer surrounding the tube on the outer surface of the eyeball 64. The filter 52 may be formed from polycarbonate, although many other materials would also be suitable such as polytetrafluoroethylene (PTFE), polyester (PETE), polypropylene, gelatin, cellulose acetate (CA), nylon, polyethersulfone (PES), regenerated cellulose (RC), or glass fiber. And as discussed earlier, valves 80, 151, or 158 for use in the drainage apparatus 20 or 68 may be formed from silicone or Silastic® material.

Other suitable filter types, valves and materials for the tube 28, inlet assembly 22, outlet assembly 34, and one-piece outlet assembly 70 of drainage apparatus 20 or 68 may be used in accordance with the present invention and will be apparent to those of skill in the art.

FIGS. 20A and 20B illustrate an alternative preferred embodiment for a valve and filter assembly, indicated generally at 132. A valve 134 includes a central chamber 136 with a drainage aperture 138 disposed therein. A filter 140 extends across an underside of the valve 134 to enclose a generally U-shaped space. An elastic member 142 having an elastic opening 144 therethrough is disposed within the U-shaped space. When there is insufficient pressure to stretch the elastic member 142, the elastic member remains in a relaxed state, and there is no flow through the drainage aperture 138, as illustrated in FIG. 20A. However, when sufficient fluid pressure is exerted on the filter 140, the elastic member 142 will stretch, opening the elastic opening 144, and exerting upward pressure on the valve 134 until the elastic opening at least partially overlaps the drainage aperture 138. In this manner, as illustrated in FIG. 20B, the valve and filter assembly 132 promote outflow of aqueous humor at sufficient pressure.

Figure 21A:
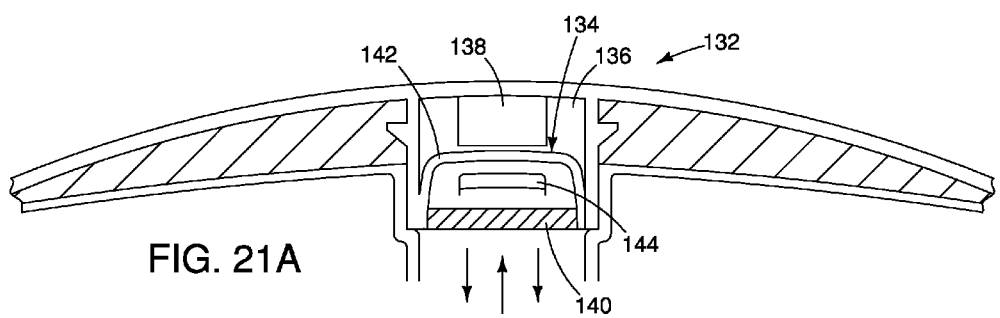
FIG. 21A is a cross-sectional view of the outlet assembly illustrated in FIGS. 2 and 3 with a valve and filter configured in a relaxed position such that aqueous humor is not exiting to a surface of the eyeball.
Figure 21B:
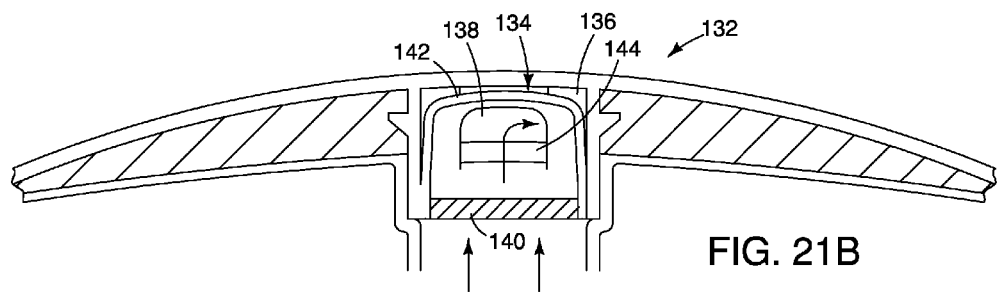
FIG. 21B is a cross-sectional view of the outlet assembly illustrated in FIGS. 2 and 3 with a valve and filter configured in a stretched position such that aqueous humor is exiting to a surface of the eyeball.

FIG. 21 illustrates still another alternative preferred embodiment for a valve and filter assembly, generally at 146. A filter 148 having areas 150 of perforations is disposed at an underside of a valve, indicated generally at 151, having four flexible flap portions 152 that are configured to open upwardly in a direction opposite the filter 148. The filter 148 provides a physical barrier to movement of the flap portions downwardly as shown, thereby restricting movement of aqueous to a unidirectional flow. The configuration of the valve 151 may comprise a greater or lesser number of flap portions and the area and size of the perforations in the filter 148 can be varied to control the flow of aqueous humor through the valve and filter assembly and therefore through the drainage aperture 138.

Figure 22:
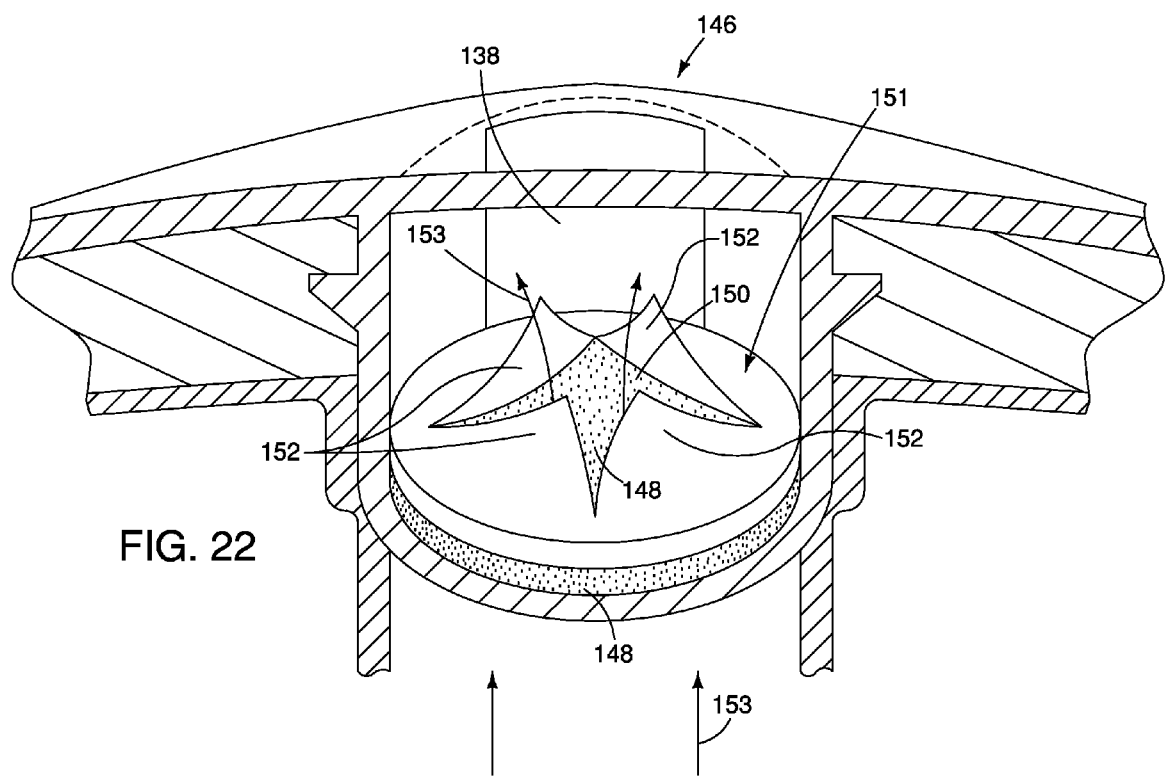
FIG. 22 is cross-sectional view of an outlet assembly with a top perspective view of a filter and valve where the filter is perforated to permit flow therethrough at sufficient fluid pressure.
Figure 23:
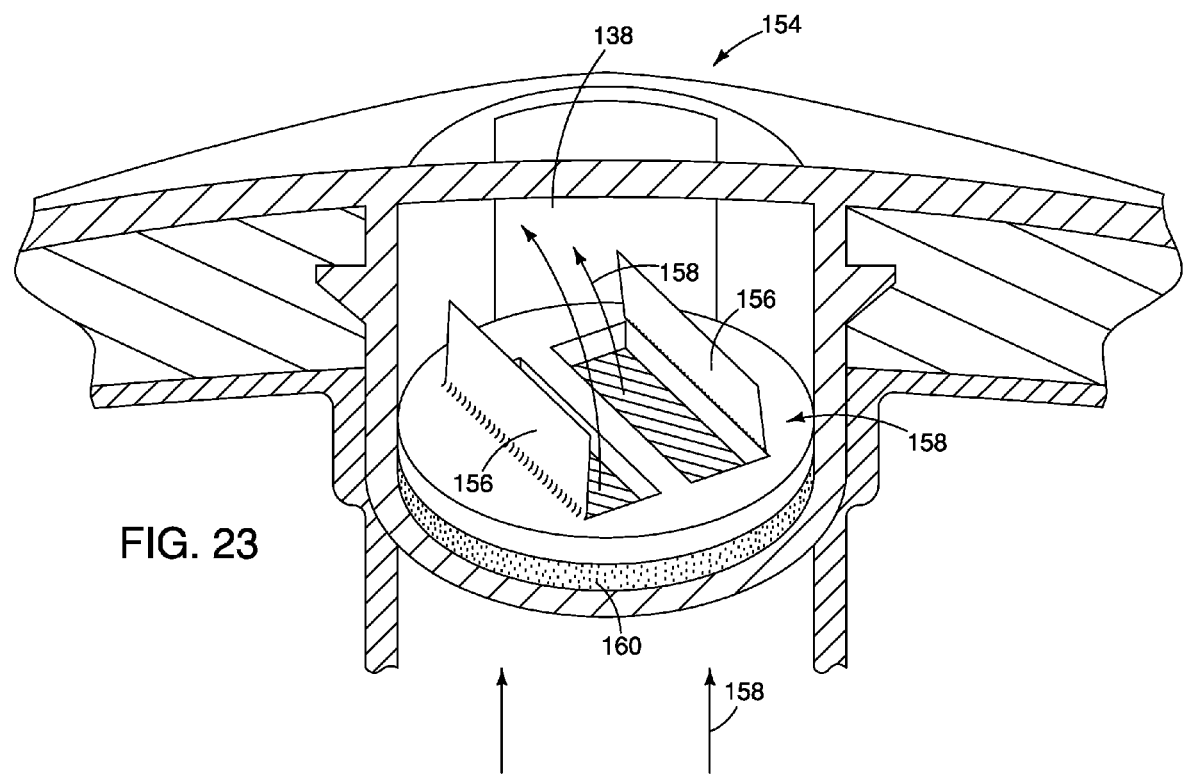
FIG. 23 is an alternative preferred embodiment of the filter of FIG. 22.

FIG. 22 illustrates yet another alternative preferred embodiment for a valve and filter assembly, generally at 154. One or more doors 156 are disposed on a top surface 155 of valve assembly 154. A filter 160 disposed beneath the top surface 155 which ensures unidirectional opening of the doors 156 under sufficient fluid pressure to permit flow of aqueous humor (shown by arrows 157) through the doors 156 and subsequently through the drainage aperture 138.

It is also highly desirable to apply coatings of solutions of one or more medicinal agents to the micropore filter 52 or to a semi-permeable membrane provided adjacent the filter for the purpose of reducing the possibility of infection, the formation of fibrosis tissue, and/or clotting. Incorporation of antimicrobial agents, as well as anti-scarring, fibrinolytic, anti-coagulant, and anti-inflammatory agents within the filter can be provided to reduce the chances of contamination or obstruction of the filter. The coatings of the agents either remain in the surface of the micropore filter, or may be absorbed into filter (the filter acting like a sponge) based on osmotic pressure. Once the agents are "washed out" or are otherwise depleted, the filter 52, 160, 148 and 140 can be replaced with a new one if desired.

One agent that is desirable is one that combats fibroblast proliferation which is a type of cell involved in wound healing which contributes to scar formations (fibrosis), is 5-fluorouracil (5-FU, anti-scarring agent that inhibits fibroblast proliferation). It is preferred that it is absorbed by the filter 52. Another anti-scarring agent that can be used instead of the 5-FU above is mitomycin C (MMC).

Both 5-FU or MMC are preferred and have been shown to be effective anti-scarring agents. Other anti-scarring agents that can be used include collagenases which are enzymes that catalyze the hydrolysis of collagen and gelatin to prevent scarring.

Another agent that can be added to the filter and the outlet assembly to prevent bacterial adhesions and operates as an anti-coagulant agent is heparin which has been used to coat intraocular lenses (IOLs) to reduce membrane formation. Heparin-sodium has been shown to reduce inflammation post-operatively.

Anti-inflammatory agents can also be applied to the filter including steroids such as triamcinolone or one of four essentially equivalent maximum-efficacy steroids: loteprednol etabonate 0.5% (Lotemax), 1% prednisolone acetate (Pred Forte), 1% prednisolone sodium phosphate (Inflamase Forte) or 1% rimexolone (Vexol) for moderate to severe inflammation; and fluorometholones for mild to moderate inflammation. Prednisolone acetate 1% (Pred Forte) is the most commonly prescribed and clinically proven topical steroid. Its chemical properties and relatively high concentration give it the greatest anti-inflammatory efficacy of all topical ophthalmic steroids. Fluorometholone alcohol (FML or Fluor-Op) is a well-known, moderate-strength ophthalmic suspension. It is commonly used to treat a host of mild to moderate ocular surface inflammatory conditions. It is also a useful drug in treating chronic inflammations requiring long-term (i.e., beyond three to four weeks) therapy. Fluorometholone alcohol's value in chronic care lies in its reduced tendency to cause secondary intraocular pressure (IOP) increase. Although chronic use of any steroid can result in increased IOP, the fluorometholone class of steroids is less likely to do so. The site-specific loteprednol may even be safer with regard to its IOP-sparing effect.

The presence of these agents within the filter enable the agents to migrate or leach out of the filter and contact the outer surface of the eye as the aqueous exits through the filter where they can perform their intended function.

In addition, coatings on the surface of the device can be helpful to prevent biofilm formations. Such coatings include: RNA III inhibiting peptide (inhibits cell-cell communication, leading to prevention of their adhesion and virulence); ionized fluoroplastic coatings (resistant to bacterial adhesion); selenium coatings (prevents the normal buildup of bacteria, film, and deposits on lenses); polyethylene glycol (provides physical, chemical, and biological barriers to the nonspecific binding of proteins, bacteria, and fibroblast cells); and/or polyelectrolyte (promotes protein and cell immobilization).

Use of the present invention as a means to treat glaucoma will allow for maintenance of a predictable post-surgical intraocular pressure which can be further modified as necessary to achieve a desired result. The present invention is comfortable and durable, and reduces the possibility of further damage to the optic nerve and visual loss resulting from excessively high or low intraocular pressure. The present invention also lessens the need for additional treatments or surgical procedures and their inherent risks, procedures which may result in further damage to vision. The insertion procedure for the present invention is far less invasive than other surgical procedures, including the procedures for inserting other drainage devices currently used to increase aqueous humor drainage. In addition, the present invention limits the risk of infection for the patient by providing an absolute barrier against infection compared with the cystic, thin-walled blebs that often occur with standard filtration procedures performed in conjunction with anti-scarring agents such as mitomycin C or 5-fluorouracil.

Various features of the invention are set forth in the following claims.

What is claimed is:

1. A drainage apparatus to reduce intraocular pressure in an eyeball that includes an anterior chamber having aqueous humor disposed therein, a cornea and a surrounding marginal limbus by which the cornea is continuous with a scleral layer and a conjunctival layer disposed on an exposed surface of the eyeball and under eyelids, said apparatus comprising:
   an inlet assembly configured to be disposed at the anterior chamber of the eyeball;
   an outlet assembly configured to be disposed at the external surface of the eyeball, said outlet assembly comprising inner and outer convex members;
   said inner and outer convex members being separated, thereby providing openings to allow aqueous humor to exit around an outer periphery thereof onto the external ocular surface, said inner and outer convex members being configured to generally correspond to the external surface of the eyeball, said inner member having a central cavity disposed therein and said outer member having a central chamber and at least one aperture disposed therein, where said central cavity and said central chamber are configured to matingly engage one another;
   a tube extending between said inlet and outlet assemblies and configured to promote fluid communication between said inlet and outlet assemblies; and
   control structure disposed within said outlet assembly for controlling a flow of aqueous humor through said tube from said anterior chamber of the eyeball to said external surface of the eyeball;
   said control structure further comprising a replaceable filter disposed within said central chamber of said outer convex member, said replaceable filter having a medicinal agent applied thereto for preventing occlusion or bacterial contamination of the replaceable filter by inhibiting at least one of the formation of fibrotic membranes or other extracellular matrix formations which can occlude the replaceable filter and lead to increased intraocular pressure or infection, said outer convex member being configured to be removable to facilitate removal and replacement of said replaceable filter without removing said inner convex member.

2. The apparatus as defined in claim 1 wherein said medicinal agent is for preventing the formation of fibrosis.

3. The apparatus as defined in claim 2 wherein 5-fluorouracil (5-FU) is applied to the filter.

4. The apparatus as defined in claim 2 wherein mitomycin C (MMC) is applied to the filter.

5. The apparatus as defined in claim 1 wherein said medicinal agent is for preventing inflammatory membrane on the filter, and further comprises high efficacy steroids.

6. The apparatus as defined in claim 5 wherein said steroids are selected from the group consisting of triamcinolone.

7. The apparatus as defined in claim 1 wherein said medicinal agent is for preventing bacterial and membranous adhesions, and further comprises heparin.

8. The apparatus as defined in claim 7 wherein said medicinal agent for preventing bacterial adhesions is coated on the outlet assembly.

9. The apparatus as defined in claim 1 wherein said medicinal agent is a tissue plasminogen activator.

10. The apparatus as defined in claim 1 wherein said medicinal agent is a collagenase.

11. The apparatus as defined in claim 1 wherein said medicinal agent is for preventing inflammatory membrane on the filter, and further comprises inhibitor to vascular endothelia growth factor (anti-VEGF).

12. The apparatus as defined in claim 11 wherein said vascular endothelia growth factor inhibitor (anti-VEGF) is selected from the group consisting of bevacizumab or ranibizumab.

13. The apparatus as defined in claim 1 wherein the inlet assembly and the tube are formed as one continuous unit.

14. The apparatus as defined in claim 1 wherein said replaceable filter is comprised of polycarbonate.

15. The apparatus as defined in claim 1 wherein a porosity of said replaceable filter is configured to selectively optimize a flow of aqueous humor.

16. The apparatus as defined in claim 1 wherein said control structure comprises a pressure-sensitive valve for providing a predetermined amount of resistance to control a flow of aqueous humor through said outlet assembly.

17. The apparatus as defined in claim 1 further comprising a replaceable valve disposed between said replaceable filter and said at least one aperture of said central chamber.

18. The apparatus as defined in claim 1 further comprising a plurality of spacers located between said inner and outer convex members to enable aqueous humor to flow from said central chamber to the outer periphery, the openings of said outlet assembly being distributed around the outer periphery thereof through which aqueous humor can exit to the external surface of the eyeball.

19. The apparatus as defined in claim 18 wherein said spacers are formed with said inner convex member and are pie shaped with adjacent spacers being spaced apart from one another to define said flow paths.

20. The apparatus as defined in claim 18 wherein one of said inner and outer convex members has said openings.

21. The apparatus as defined in claim 18 wherein said openings comprise a plurality of elongated slots.

22. A drainage apparatus to reduce intraocular pressure within an eyeball, the eyeball having aqueous humor, a curved external surface having multiple points of ingress disposed thereon, and an anterior chamber, a conjunctival layer and a limbus, said apparatus comprising:

an inlet assembly disposed within the anterior chamber for ingress of aqueous humor from the anterior chamber;

an outlet assembly disposed externally to the eyeball for draining aqueous humor exterior to the eyeball, said outlet assembly comprising inner and outer convex members with a central chamber located in one of said inner and outer convex members, said inner and outer convex members having a space between them, thereby providing openings to allow aqueous humor to exit around the outer periphery thereof onto the external ocular surface, said members being configured to matingly engage one another, said outer convex member being removable from said inner convex member, and said inner convex member abutting the external surface of the eyeball;

a conduit for conducting a flow of aqueous humor between said inlet assembly and outlet assembly;

control structure for controlling the flow of aqueous humor between said inlet assembly and outlet assembly, said control structure disposed within said central chamber and comprising a replaceable filter and a replaceable valve, said replaceable filter having a medicinal agent applied thereto for preventing occlusion or bacterial contamination of the replaceable filter by inhibiting at least one of the formation of fibrotic membranes or other extracellular matrix formations which can occlude the replaceable filter and lead to increased intraocular pressure or infection; and an anchor structure for preventing extrusion of said apparatus.

* * * * *